(12) United States Patent
Kovatchev et al.

(10) Patent No.: US 8,585,593 B2
(45) Date of Patent: Nov. 19, 2013

(54) METHOD, SYSTEM, AND COMPUTER PROGRAM PRODUCT FOR THE DETECTION OF PHYSICAL ACTIVITY BY CHANGES IN HEART RATE, ASSESSMENT OF FAST CHANGING METABOLIC STATES, AND APPLICATIONS OF CLOSED AND OPEN CONTROL LOOP IN DIABETES

(75) Inventors: Boris P. Kovatchev, Charlottesville, VA (US); Marc D. Breton, Charlottesville, VA (US)

(73) Assignee: University of Virginia Patent Foundation, Charlottesville, VA (US)

(*) Notice: Subject to any disclaimer, the term of this patent is extended or adjusted under 35 U.S.C. 154(b) by 1123 days.

(21) Appl. No.: 12/516,044

(22) PCT Filed: Nov. 27, 2007

(86) PCT No.: PCT/US2007/085588
§ 371 (c)(1),
(2), (4) Date: May 22, 2009

(87) PCT Pub. No.: WO2008/067284
PCT Pub. Date: Jun. 5, 2008

(65) Prior Publication Data
US 2010/0057043 A1   Mar. 4, 2010

Related U.S. Application Data

(60) Provisional application No. 60/861,217, filed on Nov. 27, 2006, provisional application No. 60/919,103, filed on Mar. 20, 2007, provisional application No. 60/982,251, filed on Oct. 24, 2007.

(51) Int. Cl.
*A61B 5/05* (2006.01)

(52) U.S. Cl.
USPC ............................ 600/365; 600/345; 600/347

(58) Field of Classification Search
USPC ......... 600/309, 316, 345–347, 365, 300–301; 435/4, 14; 436/68; 422/50, 420–429; 204/403.01–403.15; 702/23; 604/64–66, 48, 500–504
See application file for complete search history.

(56) References Cited

U.S. PATENT DOCUMENTS

| | | | |
|---|---|---|---|
| 6,572,542 B1 * | 6/2003 | Houben et al. | 600/300 |
| 2003/0208113 A1 * | 11/2003 | Mault et al. | 600/316 |
| 2004/0193025 A1 * | 9/2004 | Steil et al. | 600/316 |
| 2007/0248540 A1 * | 10/2007 | Hellerstein | 424/1.61 |
| 2008/0306353 A1 * | 12/2008 | Douglas et al. | 600/301 |

\* cited by examiner

*Primary Examiner* — Michael D'Angelo
(74) *Attorney, Agent, or Firm* — Novak Druce Connolly Bove + Quigg LLP; Vincent M DeLuca; Robert J. Decker

(57) ABSTRACT

A method, system, and computer program product related to the detection of physical activity using changes in heart rate. The method, system, and computer program product evaluates short term glucose demand and long term insulin action due to physical activity. The method, system, and computer program product is further related to the improvement of open and closed loop control of diabetes by accounting for the metabolic changes due to physical activity. The method, system, and computer program product is directed to detecting in real time the short and long term effects of physical activity on insulin action via heart rate analysis, and recommending changes in insulin dosing to compensate for the effects of physical activity. With these recommendations, the open and closed loop control of diabetes can be improved and steps can be taken to prevent hypoglycemia that may result from increased insulin sensitivity due to physical activity.

243 Claims, 11 Drawing Sheets

METHOD, SYSTEM, AND COMPUTER PROGRAM PRODUCT FOR THE DETECTION OF PHYSICAL ACTIVITY BY CHANGES IN HEART RATE, ASSESSMENT OF FAST CHANGING METABOLIC STATES, AND APPLICATIONS OF CLOSED AND OPEN CONTROL LOOP IN DIABETES

GOVERNMENT SUPPORT

Work described herein was supported by Federal Grant No. RO1 DK 51562, awarded by National Institutes of Health. The United States Government has certain rights in the invention.

RELATED APPLICATIONS

The present application is a national stage filing of International Application No. PCT/US2007/085588, filed Nov. 27, 2007, which claims priority under 35 U.S.C. §119(e) from U.S. Provisional Application Ser. No. 60/861,217, filed Nov. 27, 2006, entitled "Method, System, and Computer Program Product for Closed-loop Control in Diabetes During Fast Changing Metabolic States Reflected by Changes in Heart Rate," U.S. Provisional Application Ser. No. 60/919,103, filed Mar. 20, 2007, entitled "Method, System, and Computer Program Product for Closed-loop Control in Diabetes During Fast Changing Metabolic States Reflected by Changes in Heart Rate," and U.S. Provisional Application Ser. No. 60/982,251, filed Oct. 24, 2007, entitled "Method, System, and Computer Program Product for Closed-loop Control in Diabetes During Fast Changing Metabolic States Reflected by Changes in Heart Rate," the entire disclosures of which are hereby incorporated by reference herein in their entirety.

FIELD OF INVENTION

The present system relates generally to the art of open and closed loop control systems for the control of diabetes, and more importantly to the assessment of changes in insulin sensitivity.

BACKGROUND OF THE INVENTION

Recent advancements in diabetes technology include two parallel rapidly evolving areas: insulin delivery devices (subcutaneous or implanted insulin pumps) and continuous glucose monitors (CGM) recording frequent glucose determinations. So far, these two types of devices have not been linked successfully in a closed-loop glucose control system, e.g. artificial pancreas, which has the potential to dramatically improve blood glucose (BG) control, advance the quality of diabetes care, and help prevent costly complications of diabetes. Arguably, a minimally-invasive subcutaneous, SC-SC closed loop would have greatest potential for everyday use. Currently, there are five available SC CGM devices and several SC insulin pumps. A major challenge to a reliable external closed-loop control based on CGM and SC insulin injection remains the development of optimal control algorithms. A major obstacle to optimal control are two time delays inherent with SC systems: (i) the CGM resides in interstitial fluid and there exists a 5-20 minute time lag due to blood-to-interstitial glucose transport and sensor limits, and (ii) a change in the rate of insulin delivery takes ~30 minutes to result in change in insulin action. While these time delays have little impact in steady metabolic states (e.g. during sleep), they are critical during rapidly changing metabolic demands, such as meals and physical activity.

Physical activity is recognized as a major trigger of potentially dangerous hypoglycemia. While patients may ingest glucose to compensate for acutely higher demand during exercise, the long-term (several hours) increase in insulin sensitivity attributed to exercise typically remains hidden. In addition, in automated closed loop, both the acute and long-term effects of physical activity will need to be handled without assistance. However, physical activity cannot be reliably detected via glucose monitoring alone because counterregulatory and other processes delay the BG fall. As a result, in most instances, a control algorithm relying on CGM data alone, would fail to reduce the insulin infusion in a timely way and would risk inducing hypoglycemia.

An additional input beyond BG is needed to detect the onset and magnitude of physical activity. A logical candidate for such a data input is heart rate (HR). Thus, the technology proposed regarding various aspects of the present invention meets an important need and provides the capability to overcome a major obstacle to closed-loop control—the inability to account for metabolic changes due to physical activity—by providing an additional information source through HR analysis.

During the past 10 years we have developed an array of mathematical methods describing the pathophysiology of Type 1 and Type 2 diabetes (T1DM, T2DM) at several system levels, from glucose-insulin control network to self-treatment behavior. Recently we have established collaboration with Prof. Claudio Cobelli, University of Padova, Italy, who has long-standing high visibility in the field of modeling glucose dynamics and is one of the authors of the now classic Glucose Minimal Model of Glucose Kinetics (MMGK).

Aspects associated with various embodiments of the present invention achieves, but not limited thereto, the following method, system and computer program product having the following objective: quantitatively describe the effects of physical activity on glucose-insulin dynamics in T1DM and develop an algorithm detecting via heart rate analysis the short-term and long-term changes in insulin sensitivity resulting from exercise. The method, system and computer program product may utilize the proposed algorithm that would have applications in both open-loop control systems providing feedback about metabolic state to the patient, and in fully automated closed-loop artificial pancreas.

Insulin Sensitivity:

The dynamics of interstitial concentrations of insulin and glucose has been mathematically characterized by Bergman and Cobelli's now classic MMGK [2],[3], and in a number of subsequent studies [4]-[10]. As a result, excellent methods exist for quantitative assessment of insulin sensitivity in a laboratory [4] and in an outpatient setting from oral glucose tolerance test (OGTT) [7]. The MMGK allows estimation of insulin sensitivity (SI) and insulin action (X) from intravenous tests (FIG. 1). Dr. Cobelli's group has been at the forefront of these investigations, with more than 200 publications addressing various aspects of glucose-insulin dynamics in health and disease, including estimates of postprandial glucose dynamics [13]-[17]. Usually the model is numerically identified by nonlinear least squares or maximum likelihood methods, however more sophisticated approaches in healthy and T2DM subjects have been used as well [19],[20]. The potential for adding a glucose tracer allowing the segregation of insulin action on periphery vs. the liver, has been investigated as well [20].

The MMGK is designed to mimic physiology via two ordinary differential equations: one governing the dynamics of glucose (considered to be a unique compartment G), another governing the dynamics of remote insulin action (compartment X). In these equations (presented below) $S_G$ represents the balance between liver production/clearance and insulin independent utilization, linearized around a basal glucose value $G_b$; X represents the insulin dependent glucose clearance; and Ra(t) the external input of glucose (meal or IV injection). The insulin dependent clearance is also a linear simplification around the basal insulin level $I_b$, and insulin sensitivity is defined as gain of the second equation:

$$S_I = \frac{p_3}{p_2}.$$

$$\begin{cases} \dot{G} = -S_G(G - G_b) - X \cdot G + \frac{Ra(t)}{V} \\ \dot{X} = -p_2 X + p_3(I - I_b) \end{cases} \quad \text{Eq. 1.1}$$

Effect of exercise on glucose homeostasis: Optimal meal management requires the injection, in a timely fashion, of enough insulin to return to target blood glucose value within minimum time, avoiding hypoglycemia. The challenge with physical activity is different in that we are not reacting to a system perturbation (such as glucose entering the blood via the GI track) but to transient changes in the parameters of glucose/insulin dynamics, which lead to increased effectiveness of insulin [21], and potentially to hypoglycemia. These changes are well known, though not always precisely quantified, and revolve mostly around changes in glucose transport through the cell membrane and vascular changes (FIG. 2). Exercise has been shown to augment the availability of the glucose transporter GLUT-4, both by translocation to the cell membrane [22]-[24] and increased transcription in muscle cells [25],[26]. These changes have been shown to be associated with an increase in insulin sensitivity and insulin independent glucose uptake [21],[24],[27],[28]. The pathways of exercise-induced translocation and augmented transcription are not entirely elucidated yet; but muscle fibers contractions have been proven to be at the source of these changes [28]. Though abundantly studied, the effects of exercise on glucose/insulin dynamics have been primarily approached in medical and biological terms. Concepts such as glucose transporter translocation, insulin sensitivity increase, or changes in transcription of transporters have been shown but never with a quantitative approach in mind. It is not to say that models have not been used to study these phenomena—there are numerous examples in the literature of studies using different versions of the MMGK to compare the glucose dynamics pre and post exercise [21],[27],[29]-[33]. However, real-time detection of the short- and long-term effects of physical activity on insulin sensitivity has not been accomplished.

Heart rate is a natural marker of physical activity due to its availability in the field and strong link with exercise duration and intensity [37]. Other metrics could be better suited to measure exercise intensity (e.g. $V_{O2max}$ and lactate threshold) and are tightly related to qualitative change in exercise physiology [38], but they are difficult to measure in field conditions. Considering the strong linear relationship displayed between maximum heart rate and $V_{O2max}$ [39], the proposed invention uses the difference between HR and a basal measure (minimum HR at rest) as a marker of exercise.

SUMMARY OF THE INVENTION

Closed loop systems have been proven difficult to apply in clinical diabetes management, for both technical and physiological reasons. The automatic injection of insulin in patients with Type 1 diabetes (T1DM), a timely and adapted response to changing blood glucose levels, is naturally impaired by erroneous, or delayed, blood glucose reading, and technological delays in exogenous insulin action. For these reasons, simple model-independent control algorithms, such as PID controllers, have insofar failed to provide reliable, safe, automatic control of T1DM. Though more promising and more complex, model-predictive control (MPC) algorithms are still in development phase and are unable to tackle major daily life challenges, such as meals and physical activity. One of the reasons these algorithms (both PID and MPC) fail to provide a robust closed loop system is the inconsistent nature of the physiological reaction to insulin. This reaction is quantified by the well known index Insulin Sensitivity (SI), derived from the Bergman-Cobelli minimal model of glucose kinetics. The problem is that the SI changes rapidly with any system disturbance and many such changes are hard to detect via glucose monitoring alone. Certain changes in glucose utilization and insulin action due to meals are well modeled; the circadian rhythm of the SI is understood as well. However, the effect of physical activity, and more importantly its quantifying, is largely unknown. An aspect of various embodiments of the present invention method, system and computer program product to be included in open- and closed-loop systems may comprise, but not limited thereto, the following:

The addition of heart rate (HR) monitoring;

The detection of physical activity, its duration and intensity, through HR and glucose changes;

The modeling of changes in glucose uptake due to physical activity, in potentially two phases:

A short-term phase corresponding to increased glucose utilization during physical activity and shortly (1-2 hours) after;

A long-term phase (hours-to-days) corresponding to changes in insulin sensitivity and glucose replenishment triggered by prolonged intense physical activity;

The computing of recommended changes in insulin dose compensating for the effects of physical activity on insulin sensitivity.

In summary, an aspect of various embodiments of the present invention method, system and computer program product may focus on, but not limited thereto, the changes in glucose/insulin dynamics in T1DM during and after exercise and their quantification via mathematical modeling. Once identified and quantified these dynamics can be used to adapt insulin delivery to announced, or detected via heart rate, amount of exercise and therefore avoid under and overestimation of insulin needs. Such an optimal treatment would minimize the frequency of hypo- and hyperglycemic episodes frequently following over or under compensation for exercise, would be applicable to open-loop control treatment strategies (e.g. adaptive basal insulin and bolus patterns), and would be particularly critical in any closed-loop application relying on automated insulin delivery.

An aspect of an embodiment of the present invention provides a method (and related system and computer program product) for detecting physical activity and its effects on metabolic demand. The method (and related system and computer program product) may further comprise: detecting onset of the physical activity using changes in heart rate data. The method may further comprise acquiring heart rate data.

Further, the detection of physical activity may comprise: transforming the heart rate data; computing an index to detect physical activity based on results of the transformation; and detecting physical activity using the index and the heart rate data.

An aspect of an embodiment of the present invention provides a method (and related system and computer program product) for detecting physical activity and its effects on metabolic demand. The method (and related system and computer program product) may further comprise: evaluating effects of physical activity on glucose demand. The method may further comprise: acquiring glucose data and heart rate data. Further, the detection of physical activity may comprise: transforming the heart rate data; computing an index to detect physical activity based on results of the transformation; and detecting physical activity using the index and the heart rate data.

An aspect of an embodiment of the present invention provides a method (and related system and computer program product) for detecting physical activity and its effects on metabolic demand. The method (and related system and computer program product) may further comprise: evaluating changes in insulin sensitivity and glucose demand due to the physical activity; and indicating recommendations of insulin dosing. The method may further comprise: acquiring glucose data, insulin delivery data and heart rate data. Further, the detection of physical activity may comprise: transforming the heart rate data; computing an index to detect physical activity based on results of the transformation; and detecting physical activity using the index and the heart rate data.

A method, system, and computer program product related to the detection of physical activity using changes in heart rate. The method, system, and computer program product evaluates short term glucose demand and long term insulin action due to physical activity. The method, system, and computer program product is further related to the improvement of open and closed loop control of diabetes by accounting for the metabolic changes due to physical activity. The method, system, and computer program product is directed to detecting in real time the short and long term effects of physical activity on insulin action via heart rate analysis, and recommending changes in insulin dosing to compensate for the effects of physical activity. With these recommendations, the open and closed loop control of diabetes can be improved and steps can be taken to prevent hypoglycemia that may result from increased insulin sensitivity due to physical activity.

These and other objects, along with advantages and features of the invention disclosed herein, will be made more apparent from the description, drawings and claims that follow.

BRIEF SUMMARY OF THE DRAWINGS

The accompanying drawings, which are incorporated into and form a part of the instant specification, illustrate several aspects and embodiments of the present invention and, together with the description herein, and serve to explain the principles of the invention. The drawings are provided only for the purpose of illustrating select embodiments of the invention and are not to be construed as limiting the invention.

FIG. 6(B): insulin injection (blue, as identified as "insulin pump" in the graph), concentration (green as identified as "free insulin" in the graph) and action (black as identified as "remote insulin action" in the graph); FIG. 6(C): transient (blue as identified as "glucose pump" in the graph) and long term (red as identified as "Si" in the graph) changes in glucose usage.

DETAILED DESCRIPTION OF THE INVENTION

An aspect of various embodiments of the present invention method, system and computer program product comprises, but not limited thereto, the quantitative estimation of short-term and long-term changes in individual insulin sensitivity (SI) from heart rate. The computation of these changes may rely on the mathematical algorithm described below, which is derived from the classic MMGK. As shown in the literature, the parameters of the minimal model ($S_I$ but also $S_G$) can significantly change during and after physical activity [21], [34]. These changes are consequence from vascular and metabolic adaptations to increased energy utilization and storage described above, rendering the minimal model impossible to use during exercise without a precise description of the amplitude and dynamics of these changes. Moreover, without announcement, the timing of exercise is not known, making difficult any real-time exercise detection.

Figure 1:
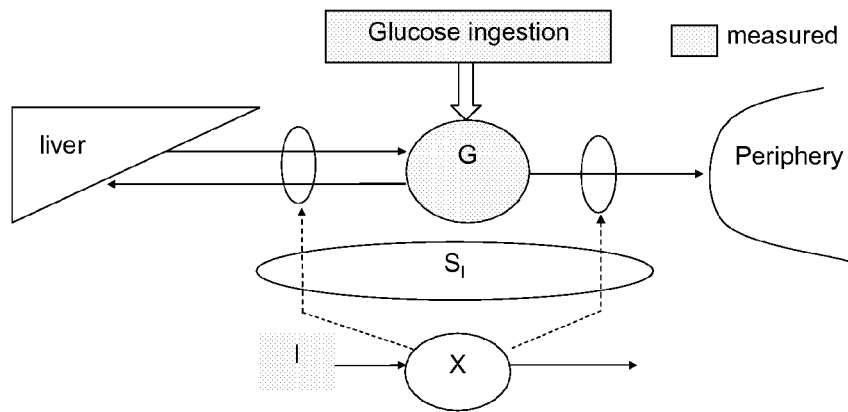
FIG. 1 provides a graphical representation of the Minimal Model of Glucose Kinetics.
Figure 2:
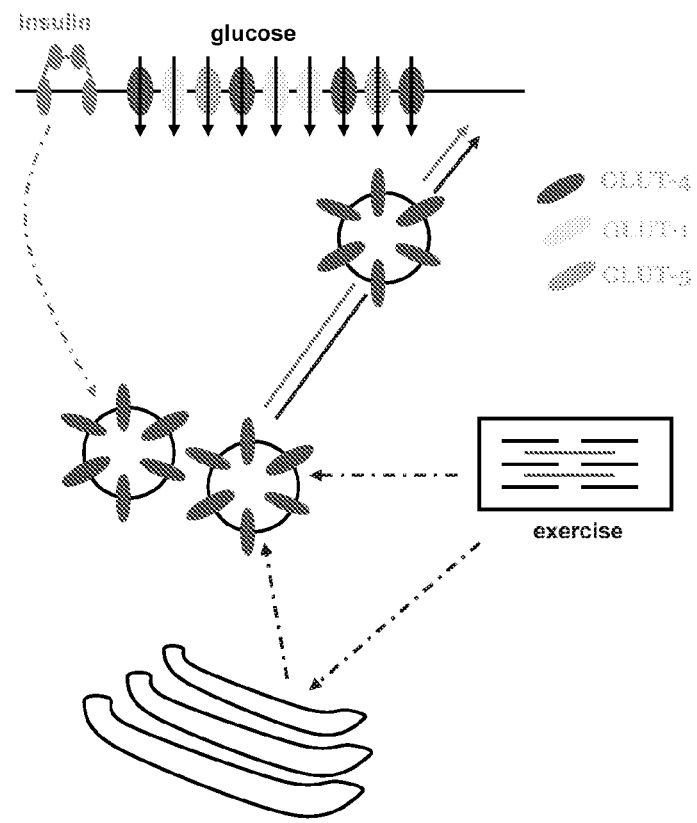
FIG. 2 provides a graphical representation of the effect of exercise on transmembrane glucose transport.
Figure 3:
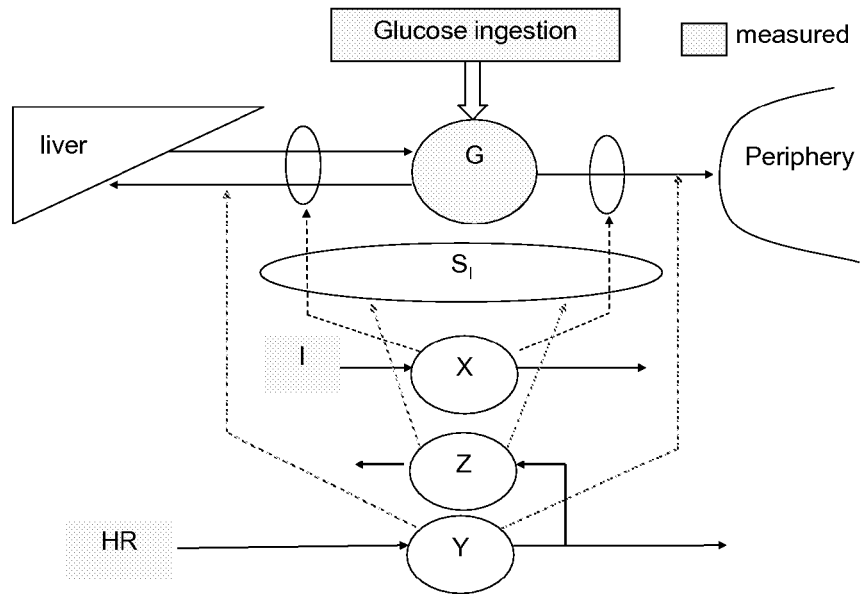
FIG. 3 provides a graphical representation of the Exercise Minimal Model of Glucose Kinetics (EMMGK).

The Exercise Minimal Model of Glucose Kinetics (EMMGK):

In a previous publication [36] we have shown that changes in glucose/insulin dynamics due to mild to moderate exercise can be described in two phases: a transient change in insulin independent glucose clearance and a longer term change in insulin sensitivity, confirming and expanding the work of Derouich et al. [34] with clinical data. The EMMGK is a model based on these studies but with no changes in model parameters. Instead we minimally augment the state of the system, using HR as a driving function. This results in the augmentation of MMGK (See FIG. 1) with two additional compartments Y and Z presented in FIG. 3.

The equations governing these compartments are:

$$\begin{cases} \dot{G} = -p_1(G - G_b) - (1 + \alpha Z + \beta Y)X \cdot G + \dfrac{D}{V_g} & (1) \\ \dot{X} = -p_2 X + p_3(I - I_b) & (2) \\ \dot{Y} = -\dfrac{1}{\tau_{HR}} Y + \dfrac{1}{\tau_{HR}}(HR - HR_b) & (3) \\ \dot{Z} = -\left(f(Y) + \dfrac{1}{\tau}\right) \cdot Z + f(Y) & (4) \end{cases} \quad \text{Eq. 1.2}$$

$$\text{where } f(Y) = \frac{\left(\frac{Y}{a \cdot HR_b}\right)^n}{1 + \left(\frac{Y}{a \cdot HR_b}\right)^n}$$

In the first equation glucose clearance is augmented during exercise via both the insulin independent (by $\alpha Y$) and insulin dependent terms (by $\beta Z$). Y is computed as $\Delta HR$ smoothed and delayed via a first order linear ordinary differential equation (ODE). Thus, Y represents the transient short-term increase in glucose uptake due to exercise. Z is controlled via a non linear ODE driven by f(Y). The function f(Y) is constructed so that it is negligible until Y reaches a certain fraction of the basal HR, corresponding to onset of exercise; f(Y) reaches 1 rapidly thereafter (speed is dependent on a and n) and drives Z upward. After exercise f(Y) resumes a negligible value, allowing Z to slowly drift back via quasi exponential decay driven by $\tau$. Thus, Z represents the long-term change in insulin sensitivity due to exercise. It should be appreciated that alternative solutions of the aforementioned equation may be implemented to achieve the objective of the present invention.

Short Term Equation

The equation below corresponds to short term changes in glucose demand and short term changes in glucose demand and insulin action:

$$\begin{cases} \dot{G} = -p_1(G - G_b) - (1 + \beta Y)X \cdot G + \dfrac{D}{V_g} & (1) \\ \dot{X} = -p_2 X + p_3(I - I_b) & (2) \\ \dot{Y} = -\dfrac{1}{\tau_{HR}} Y + \dfrac{1}{\tau_{HR}}(HR - HR_b) & (3) \end{cases} \quad \text{Eq. 1.3}$$

where G represents glucose value, $G_b$ is basal glucose value, X is insulin dependent action, D represents glucose input, V is the diffusion volume, I is the insulin value, $I_b$ represents basal insulin value, Y represents the transient variation in metabolic activity, $\beta$ represents the short term metabolic demand to heart rate ratio, HR represents heart rate, $HR_b$ represents basal heart rate, $p_1$ represents the balance between liver production/demand and insulin independent glucose demand, $\tau_{HR}$ represents the lag between onset of physical activity and changes in metabolic demand, $p_2$ represents the lag between appearance of insulin and action of insulin, and $p_3$ represents the intensity of insulin action. It should be appreciated that alternative solutions of the aforementioned equation may be implemented to achieve the objective of the present invention.

Long Term Equation

The equation below corresponds to long term changes in glucose demand and long term changes in glucose demand and insulin action:

$$\begin{cases} \dot{G} = -p_1(G - G_b) - (1 + \alpha Z)X \cdot G + \dfrac{D}{V_g} & (1) \\ \dot{X} = -p_2 X + p_3(I - I_b) & (2) \\ \dot{Y} = -\dfrac{1}{\tau_{HR}} Y + \dfrac{1}{\tau_{HR}}(HR - HR_b) & (3) \\ \dot{Z} = -\left(f(Y) + \dfrac{1}{\tau}\right) \cdot Z + f(Y) & (4) \end{cases} \quad \text{Eq. 1.4}$$

$$\text{where } f(Y) = \frac{\left(\frac{Y}{a \cdot HR_b}\right)^n}{1 + \left(\frac{Y}{a \cdot HR_b}\right)^n}$$

where G represents glucose value, $G_b$ is basal glucose value, X is insulin dependent action, D represents glucose input, V is the diffusion volume, I is the insulin value, $I_b$ represents basal insulin value, Y represents the transient variation in metabolic activity, $\beta$ represents the short term metabolic demand to heart rate ratio, Z represents the long-term change in insulin sensitivity due to physical activity, $\alpha$ represents the long term change amplitude, HR represents heart rate, $HR_b$ represents basal heart rate, $p_1$ represents the balance between liver production/demand and insulin independent glucose demand, $\tau_{HR}$ represents the lag between onset of physical activity and changes in metabolic demand, $p_2$ represents the lag between appearance of insulin and action of insulin, $p_3$ represents the intensity of insulin action, $\alpha$ represents the fraction of basal heart rate above basal heart rate at which physical activity is detected, and n represents the steepness of the aforementioned threshold.

Identifying the EMMGK:

The described model is highly subject-specific: $S_I$ but also $S_G$ or $p_2$ can have up to 10-fold difference between people; therefore identifying the model parameters for a particular person critical is critical for its algorithmic application. To estimate the model parameters we first assume that blood glucose, blood insulin, and heart rate are available. In this case, we fix $\tau$, $\tau_{EX}$, $\alpha$, and n to reflect published results (e.g. significant $S_I$ augmentation for up to 20 hours after exercise). Then, by recursively differentiating the model we can demonstrate that, if plasma glucose, insulin, and HR are measured, all non fixed parameters are theoretically identifiable.

Insulin Kinetics

Figure 4:
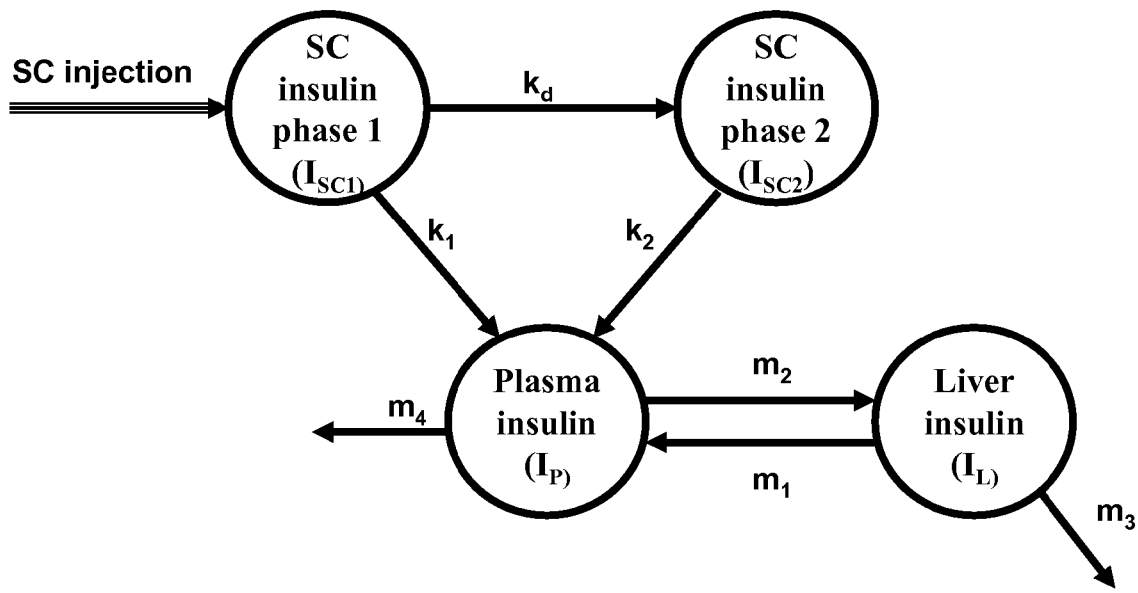
FIG. 4 provides a graphical representation of the model of insulin kinetics.

In practice, insulin concentration is difficult to measure and is impossible to measure under field conditions. Thus, we derive insulin concentration from the only available source of insulin data in T1DM—the rate of insulin infusion from the insulin pump. This extrapolation requires knowledge of the kinetics of insulin transport from subcutaneous delivery (insulin pump) to blood. Insulin kinetics can be modeled via the 2-compartment model in FIG. 4. This model was first presented by Dalla Man [45] in T2DM and health and further refined in T1DM.
The model equations are:

$$\begin{cases} \dot{I}_P = m_1 I_L - (m_2 + m_4) I_P + k_1 I_{SC_1} + k_2 I_{SC_2} \\ \dot{I}_L = m_2 I_P - (m_1 + m_3) I_L \\ \dot{I}_{SC_1} = -(k_1 + k_d) I_{SC_1} + J(t) \\ \dot{I}_{SC_2} = -k_2 I_{SC_2} + k_1 I_{SC_1} \end{cases} \quad \text{Eq. 2}$$

$$I_P(0) = I_{Pb}$$
$$I_L(0) = I_{Lb}$$
$$I(t) = I_P(t)/V_i$$
$$I_{SC_1}(0) = J_b/k_1 + k_d$$
$$I_{SC_2}(0) = k_1 I_{SC_1}(0)/k_2$$

$I_p$ denotes the insulin mass in plasma, $I_L$ the insulin mass in the Liver, and I denote the concentration of plasma insulin, therefore Vi is the diffusion volume of the plasma compartment. Suffix b denotes basal state, J subcutaneous insulin injection (pmol/kg/min), $m_1, m_2, m_4$ (min-1) rate parameters. Degradation, D, occurs both in the liver and in the periphery. Peripheral degradation has been assumed linear ($m_4$). It should be appreciated that alternative solutions of the aforementioned equation may be implemented to achieve the objective of the present invention.

Modification of Insulin Regimen Using the EMMGK.

Assuming that we have an optimal insulin injection schedule J(t), which can be a closed loop control, an open loop control, or any insulin management plan that includes a continuous injection component. Using the EMMGK we can derive an optimal adaptation to exercise of this injection schedule as follow:
Since $$\dot{G} = -p_1(G - G_b) - (1 + \alpha Z + \beta Y) X \cdot G + \frac{D}{V_g}$$

and considering we can only act on insulin, id est the value of X.
We can compute the value of X that would ensure no visible effect of exercise:

$$\tilde{X} = \frac{X}{1 + \alpha Z + \beta Y} \quad (a)$$

defining $$S_I = \frac{p_2}{p_3},$$

and CL to be the insulin clearance, we have $$X_\infty = S_I \frac{J_\infty - J_b}{CL} \quad (b)$$

where $J_b$ is the injection needed to obtain the plasma insulin concentration $I_b$ therefore, we obtain a new injection scheduled derive from equation (a) and (b)

$$S_I \frac{\tilde{J} - J_b}{CL} = S_I \frac{J - J_b}{CL(1 + \alpha Z + \beta Y)} \quad \text{Eq. 3.1}$$
$$\Rightarrow \tilde{J}(t) = \frac{J(t)}{1 + \alpha Z(t) + \beta Y(t)} + \frac{\alpha Z(t) + \beta Y(t)}{1 + \alpha Z(t) + \beta Y(t)} J_b$$

For short term insulin dosing, the following equation represents the injection schedule:

$$\tilde{J}(t) = \frac{J(t)}{1 + \beta Y(t)} + \frac{\beta Y(t)}{1 + \beta Y(t)} J_b \quad \text{Eq. 3.2}$$

where $\tilde{J}(t)$ is an optimal injection schedule adapted to physical activity at time t, J(t) is an optimal injection schedule at time t, Y(t) represents the transient variation in metabolic activity, $J_b$ is injection needed to obtain the plasma concentration $I_b$, β represents the short term metabolic demand to heart rate ratio.

For long term insulin dosing, the following equation represents the injection schedule:

$$\tilde{J}(t) = \frac{J(t)}{1 + \alpha Z(t)} + \frac{\alpha Z(t)}{1 + \alpha Z(t)} J_b \quad \text{Eq. 3.3}$$

where $\tilde{J}(t)$ is an optimal injection schedule adapted to physical activity at time t, J(t) is an optimal injection schedule at time t, Z(t) is the long-term change in insulin sensitivity due to physical activity at time t, $J_b$ is injection needed to obtain the plasma concentration $I_b$, and α is the long term change in amplitude.

Using Spectral Analysis of the First Order Difference R-R Intervals to Detect Exercise.

While spectral analysis of the RR-interval is a commonly accepted tool to characterize changes in cardiac activity during exercise [46],[47], its use as a real-time detector of physical activity has not yet been presented as part of an insulin management system. This could be in part due to the difficulty of extracting meaningful spectral information from the heart rate signal, as well as to confounding effects such as autonomic neuropathy in diabetes. While an embodiment of the present invention uses the changes in heart rate spectral characteristics, the present invention provides a novel index to detect exercise, as part of an insulin management system. The proposed index is as follow:

$$I_{EX} = \frac{\sum_{\nu > 0.15 \, Hz} P_t(\nu)}{\sum_{\nu \leq 0.15 \, Hz} P_t(\nu)} \quad \text{Eq. 4}$$

Where $P_t(\nu)$ is an estimate of the power spectrum of the first order difference of the heart rate signal at time t and frequency ν. The signal is re-sampled at equal intervals (2 Hz) for proper use of Fourier techniques, and the estimate is obtained by computing the time frequency representation of the signal on the first order difference of the RR signal, using wavelet de-noising of the TF representation, and moving average smoothing (both in time and frequency domain of width 5). It should be appreciated that alternative solutions of the aforementioned equations may be implemented to achieve the objective of the present invention.

Algorithmic Implementation of the EMMGK:

An embodiment of the method may have three principal components. Here these components are presented sequentially, however, each of them can be used separately in an implementation independent from the others:

Component 1: Exercise detector;
Component 2: Estimator of increase in metabolic demand due to physical activity;
Component 3: Recommendation of insulin dosing change to compensate for exercise.

Data and Data Pre-Processing:

The real-time detection of the changes in insulin sensitivity due to physical activity relies on the acquisition of a data stream that is available from continuous monitoring, HR monitoring, and reporting of insulin pump infusion rate. Thus:

Step 1 [components 1, 2, and 3] of the algorithm is to acquire real-time data from the following sources:
 1. CGM data, typically a time series of frequent BG determinations generated at a rate of one data point every 1 to 10 minutes;
 2. Insulin delivery data from insulin pump, including basal rate and boluses;
 3. Heart rate data from HR monitor acquired in short time intervals, e.g. 5 sec.

These three data sources are synchronized to produce a time-stamped three-dimensional time series of vectors (BG(t), I(t), HR(t)), which is submitted to the model identification procedure.

Step 2 [components 1, and 2] includes identifying of basal heart rate parameters for each individual during rest (e.g. overnight). This is the "training phase" of the method, which allows the EMMGK to be tailored to the specifics of the metabolic system of each person;
 1. $HR_b$ is defined as the overnight average heart rate.
 2. basal $I_{EX}$ ($I_{EXb}$) is defined as the average $I_{EX}$ overnigtht.

Step 3 [component 1] detection of exercise.
 1. resample last 10 minutes HR signal at 1 Hz using cubic spline
 2. compute Fast Fourier Transform (FFT) of resampled HR signal with bandwith smoothing $\omega=0.05$ Hz
 3. compute $I_{EX}$ based on FFT results.
 4. If $I_{EX}>2*I_{EXb}$ AND $HR>1.3*HR_b$, exercise is detected.

Step 4 [components 2, and 3] includes detection of deviations from basal state using HR and BG information. These deviations are quantified using the EMMGK as follows:
 1. the heart rate signal is smoothed using a Moving Average algorithm
 2. the resulting signal is used as an input in equation 3 and 4 of the EMMGK (Z and Y are initialized at 0). The differential equations are solved up to actual time.
 3. current values of Y and Z are reported.

Step 5 [component 2] includes computation of the change in metabolic demand.
 1. get actual Y and Z values
 2. insulin dependent glucose utilization is increased by $\alpha Z+\beta Y$ percents Step 6 [component 3] includes recommendation of changes in insulin delivery to account for metabolic changes in step 5. These changes are quantified as follows:
 1. For open-loop implementation:
  a. Get actual Z value
  b. Divide insulin regimen by $(1+\alpha Z)$
 2. For closed-loop implementation: Defining the actuation period (time between 2 consecutive update of the insulin injection) as $\tau$,
  a. Get actual Y and Z values
  b. Adapt closed loop insulin prescription as per equation 1.4; if $J_b$ is not available, fix $I_b$ to 0, i.e. $J_b=0$, and divide suggested injection by $(1+\alpha Z+\beta Y)$ Step 7 [component 3] is the presentation of output from the procedure described in Steps 1-to-6. The format of the output depends on the mode of application of the method as follows:
 1. For open-loop control applications, a reduction in the basal pump rate and/or reduction in the subsequent insulin bolus will be recommended to the patient in units of insulin upon detection of exercise;
 2. For automated closed-loop control application, reduced pump rate and reduced bolus amounts will be directly transmitted to the insulin pump, using online HR monitoring.

Validation of $I_{EX}$

Figure 5:
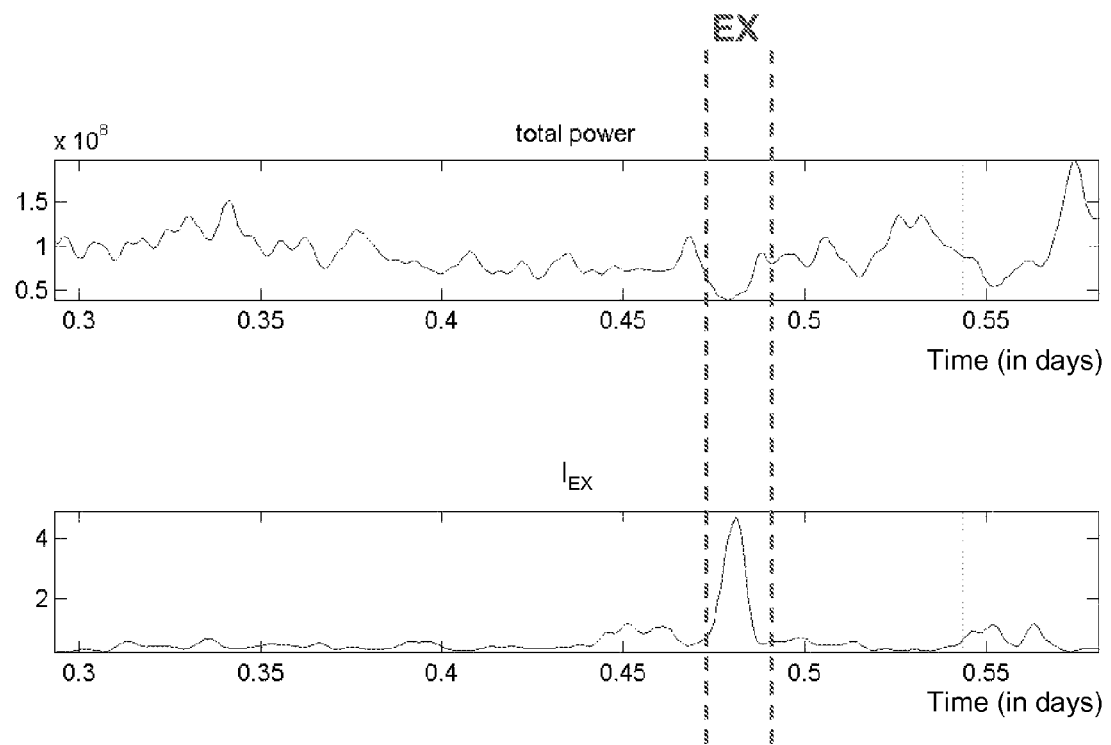
FIG. 5 provides a graphical representation of the validation of spectral index detection of exercise.

This index was computed before, during, and after a low intensity (50% $VO_{2max}$-lactate threshold) exercise bout in 35 T1DM patients, during 2 inpatient days at the General Clinical Research Center at the University of Virginia (70 traces total). While only some patients presented the expected (from literature) drop in beat to beat interval variability, see FIG. 5 top panel, almost all (79%) presented a very clear peak in the $I_{EX}$ index during physical activity. A representative trace is presented in FIG. 5, lower panel.

Validation of the EMMGK:

We have run two GCRC protocols pertaining to the effect of exercise in health and in T1DM:

Protocol #1 (GCRC code WLC015):

Subjects: Thirty-nine subjects with T1DM were recruited through regional advertisement. Exclusion criteria were age>65 years, mental retardation, psychological diagnoses or active substance abuse. The average age of the participants was 42.5 years±12, the average duration of T1DM was 21.6±9.4 years, the average HbAlc was 7.4±0.8%; there were 16 males.

Procedure: Subjects were admitted to the University of Virginia GCRC in the evening prior to the study and their BG levels were controlled overnight within the target range of 100-150 mg/dl, preventing hypoglycemia (BG<70 mg/dl). Two hyperinsulinemic clamps were performed on two consecutive days: Each clamp used constant insulin infusion rate=1 mU/kg/min and variable glucose infusion rate to achieve and maintain BG levels at approximately 110 mg/dl. Subsequently, the glucose infusion rate was reduced to permit a controlled decline in BG of approximately 1 mg/dl/min until BG reached ~50 mg/dl. Glucose infusion was then resumed to allow a recovery to normal glucose levels. The euglycemic portion of the clamp study varied in length from 70 to 210 minutes, and included 15 minutes of exercise at 50% $V_{O2max}$-lactate and a 20 minutes recovery period. The duration of the BG reduction procedure ranged from 30 to 60 minutes, the recovery ranged from 30 to 60 minutes. Because insulin was not measured during the protocol, the plasma concentration was estimated using population parameters for volume of insulin dispersion and half life of insulin in plasma. Therefore, insulin concentration is derived from injected insulin, $I_b$ "measured" as the steady state of the basal injection before the beginning of the clamp, a technique similar to the insulin kinetics model presented in the precious section.

Figure 6A:
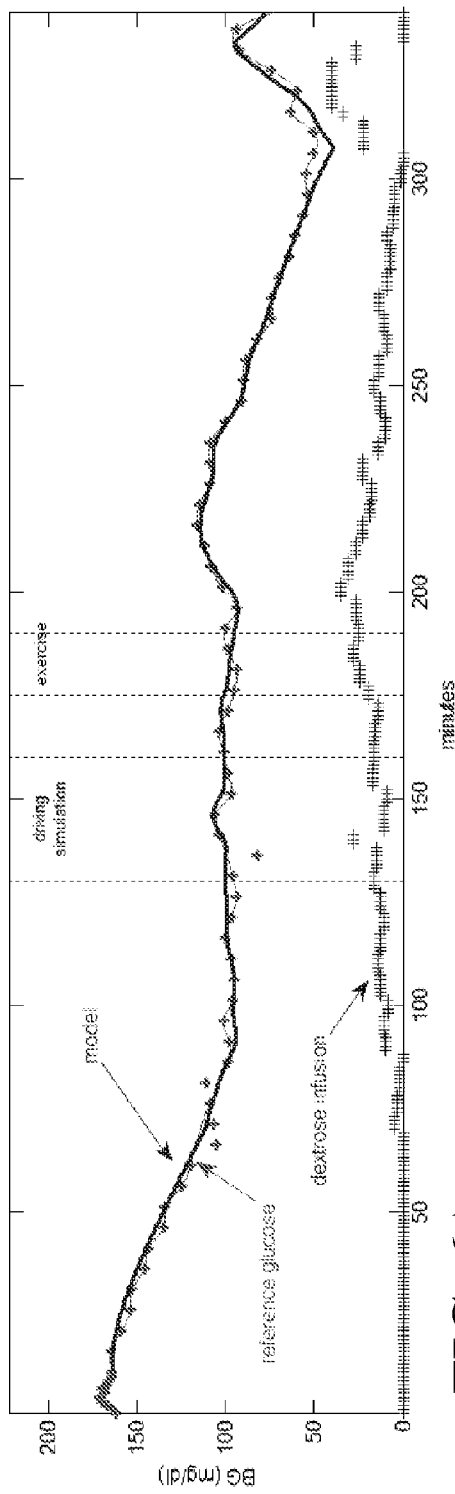
FIGS. 6(A)-(C) provide a graphical representation of the case study of changes in glucose usage due to exercise. Case study: day1 of subject 121, referring to FIG. 6(A): glucose measure (as illustrated by red cross-marks "+" having a line there through it), injection (as illustrated in blue cross-marks "+") and modeling (blue curve)
Figure 6C:
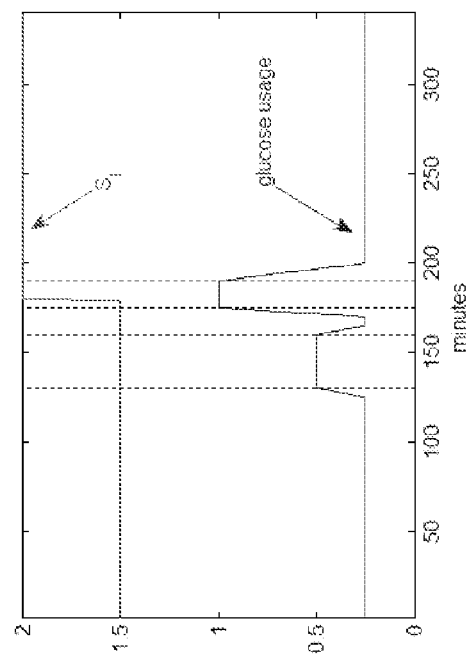
Figure 6B:
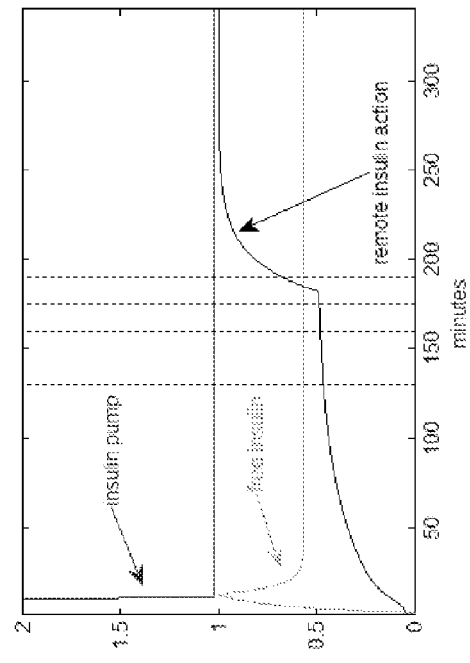

Results: As an example we present the curve of day 1 of subject 121 (FIG. 6). While the MMGK (which has fixed insulin sensitivity and glucose usage) failed to properly follow the measured glucose trace, small changes (FIG. 6, panel C) in glucose usage and insulin sensitivity during and after exercise were sufficient to explain the discrepancy (FIG. 6, panel A). We also observed that a change in glucose usage during exercise and recovery is not enough to explain the increase in dextrose infusion.

Using minimal model analysis tools, we assessed:
1. Metabolic demand computed from glucose infusion rate increased by 50% within few minutes of initiation of exercise, from 4.58 to 6.62 mg/kg/min.
2. During exercise insulin action X increased, beginning approximately 5 minutes after initiation; $p_2$ increased from pre-exercise value of 0.009 to 0.34 $min^{-1}$. The increase in $S_I$ was not significant (8.69 vs 8.86 $min^{-1}$ per μU/ml) but $S_I^D$ increased from 2.03 $10^{-4}$ to 8.43 $10^{-4}$ $min^{-1}$ per μU/ml.
3. After exercise insulin action decayed with a slower than onset rate constant $p_2$ 0.19 $min^{-1}$. $S_I$ during recovery was 7.21 $min^{-1}$ per μU/ml and $S_I^D$ 6.59 $10^{-4}$ $min^{-1}$ per μU/ml.

Figure 7:
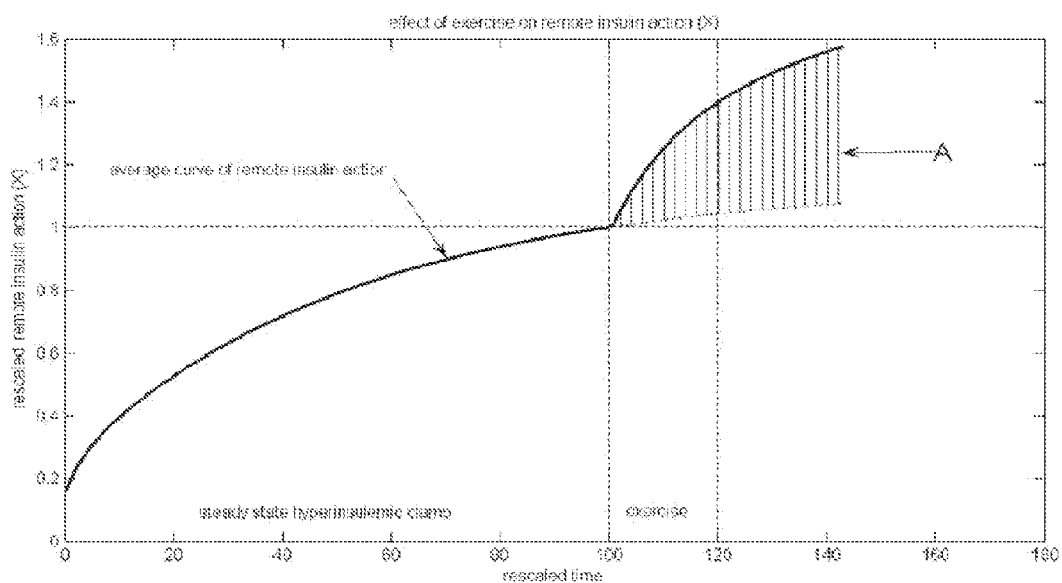
FIG. 7 provides a graphical representation of the average increase in insulin action due to exercise, illustrated by the shaded area representing the average difference between the theoretical (MMGK) and empirical insulin action.

The observed increase in insulin action is depicted in FIG. 7. The protocol did not include an observation period long enough to capture exactly the timing of recovery and the return of glucose usage to basal values. Values in the literature for such a return range between 20 and 24 hours.

Figure 8:
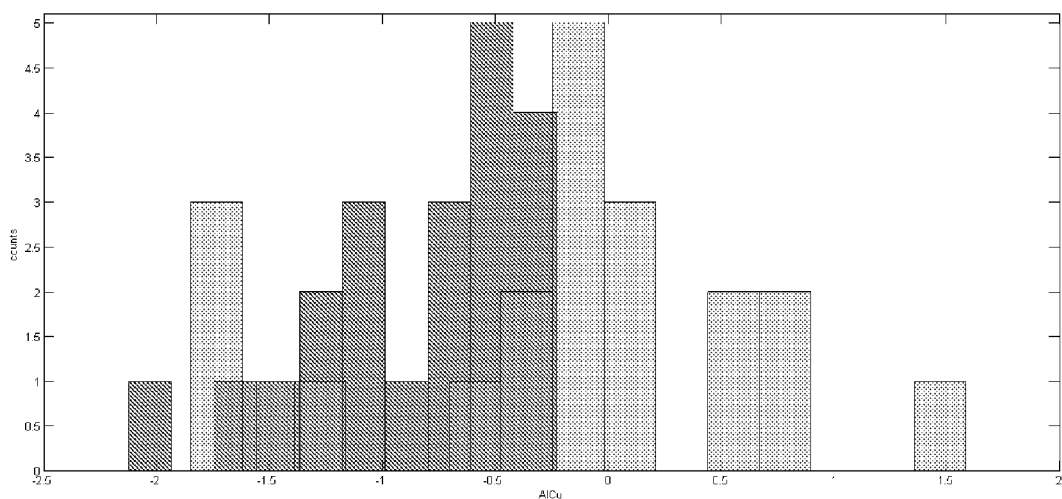
FIG. 8 provides a comparison of the classic MMGK and the new Exercise-specific model, illustrating the superiority of the EMMGK according to the Akaike information criterion. The MMGK is graphically illustrated with the bar graphs having lighter shading and the EMMGK is graphically illustrated with the bar graphs having darker shading FIG. 9 provides a graphical representation of sharp increase in glucose consumption and change in insulin secretion due to exercise. Measured samples are represented by blue as illustrated by cross marks "+" and smoothed curved are in red as illustrated by solid lines.
Figure 9:
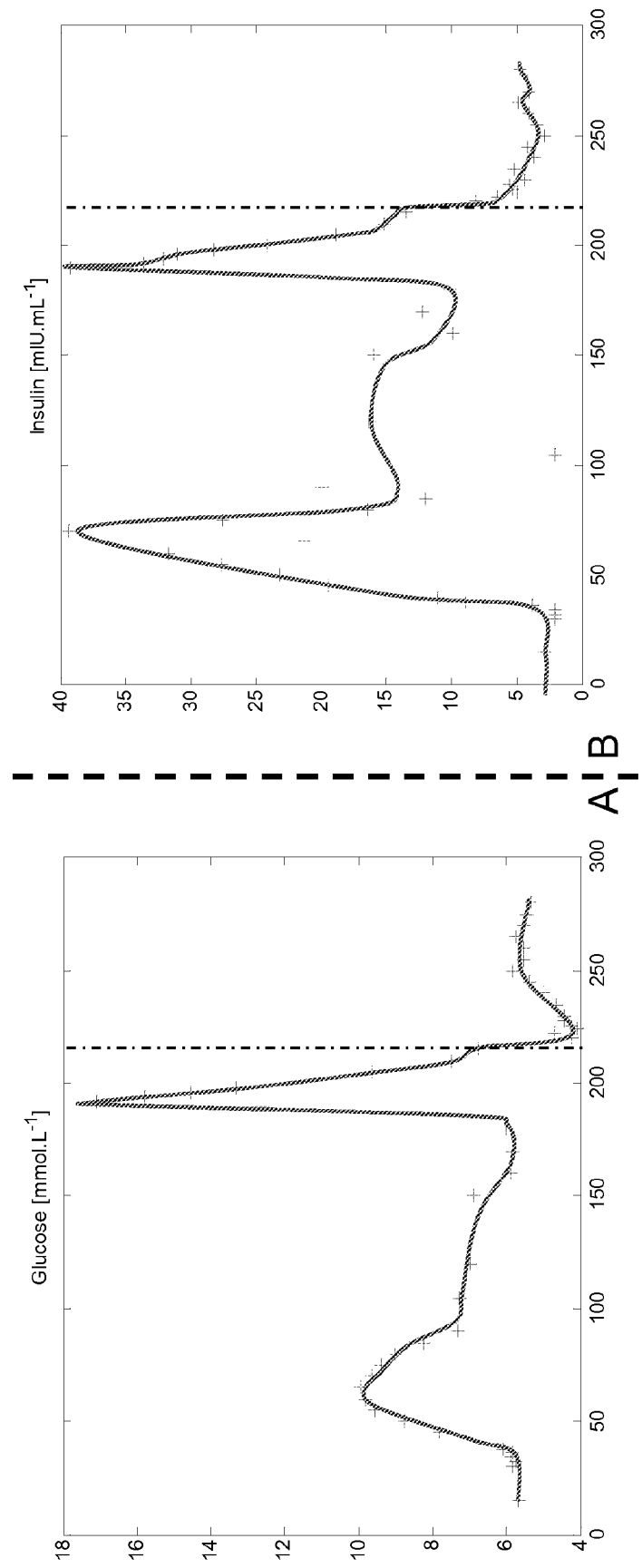

The EMMGK was able to follow glucose dynamics during and after exercise and, most importantly, to follow the descent into hypoglycemia, while avoiding unrealistic parameter values. The weighted sum of squared errors (WSSE) was significantly lower for EMMGK than for the standard MMGK (7.77 vs 18.6 p<0.01). However, comparing error of fit and parameter values is not sufficient to judge the superiority of a model, because EMMGK demands the estimation of 2 additional parameters. Therefore to fully compare EMMGK and MMGK we computed a modified Akaike information criterion (AIC) for each model and each subject. This criterion accounts for the number of parameters. The EMMGK showed significantly lower AIC values than the MMGK: −0.85 vs −0.25, p<0.05; therefore showing a significant advantage in using the EMMGK over the classic MMGK during and after exercise, as shown in FIG. 8:

Protocol #2 (GCRC code MDB001):
Subjects: The MDB001 protocol was conducted in November-December 2006 at the UVa GCRC and enrolled 10 healthy volunteers ages 18 to 35. The protocol was designed to investigate the glucose/insulin equilibrium and dynamics in health during highly unstable physiological states, namely: (i) physical activity—both low and high intensity; (ii) nutrient ingestion. Both situations are common in daily life and have been identified as major obstacles to closed loop glucose control. The research plan of MDB001 included a GCRC-based investigation of the glucose/insulin dynamics during ingested and injected glucose as well as during physical activity periods.
Procedure: To this effect the protocol included an oral glucose tolerance test (OGTT), an intravenous glucose tolerance test (IVGTT, considered a gold standard for assessment of glucose kinetics) and a 45-minute exercise period, divided into low- and high-intensity phases.
Results: Glucose traces (FIG. 9) show a very sharp decrease in glucose concentration and insulin concentration at onset of moderate exercise (minute 220), followed by counter-regulation (verified by epinephrine measurement) which brings glucose back up during the intense exercise period, and a small decrease in insulin concentration (minute 250). The results confirm the dynamics of short-term glucose increase attributed to the onset of exercise. No long-term effect of exercise on insulin sensitivity could be directly observed due to the counterregulatory response effect on $S_I$ (transient increase).

In summary, increasing scientific and industrial effort is focused on the development of closed-loop systems (artificial pancreas) to control glucose metabolism of people with diabetes, particularly T1DM. Experiments are being conducted with continuous glucose monitors (CGM) coupled with insulin pumps and a control algorithm. While such systems have proven feasible in steady metabolic states, they fail during changing metabolic demands, such as meals and physical activity. Because physical activity is a major trigger of acute hypoglycemia in diabetes, the timely detection of metabolic changes is critical for the success of closed-loop control. However, increased metabolic demand due to physical activity cannot be reliably detected via glucose monitoring alone.

An aspect of various embodiments of the present invention comprises, but not limited thereto, a method, system, computer program product, device and apparatus using changes in heart rate (HR) as a correlate to increased metabolic demand. Specifically, the invention consists of three algorithms: (i) detecting physical activity, its duration and intensity through HR; (ii) quantifying short-term and long-term changes in insulin sensitivity due to physical activity, and (iii) computing recommended changes in insulin dose to compensate for the effects of physical activity on insulin sensitivity.

An aspect of the present invention technology and related method provides the capability to overcome one of the major limitations of open-loop and closed-loop control of diabetes—the inability to account for metabolic changes due to physical activity—by providing an additional information source through heart rate monitoring.

Continuous monitoring devices are rapidly developing and it is expected that they will become soon essential part of the mainstream treatment of diabetes. Insulin infusion pumps are on the market, and the first systems providing open-loop control have been approved by the FDA (The Paradigm system by Medtronic Minimed, Nortridge, Calif.). Because the metabolic changes due to physical activity are a major obstacle to optimal open-loop or closed-loop glucose control, this invention will provide numerous advantages. An aspect of various embodiments of the present invention may provide a number of advantages, such as but not limited thereto, the following: automated detection of the onset of physical activity using changes in heart rate; quantitative evaluation of short-term changes in insulin sensitivity during and shortly after physical activity; quantitative evaluation of long-term changes in insulin sensitivity following exercise; recommendations for changes in insulin dose corresponding to the changes in insulin sensitivity in open-loop control systems and patient advisory systems; and automated real-time suggestion of changes in insulin basal rate and boluses in closed-loop control systems.

Standard clinical practice includes recommendation for lowering insulin dose in T1DM prior to or during exercise. However, none of these recommendations based on direct evaluation of changes in insulin sensitivity. There is no field-based assessment of these changes; and in general there are no treatment recommendations using heart rate monitoring for any aspect of the treatment of diabetes.

An aspect of various embodiments of the presentation invention may provide a number of advantages, such as but not limited thereto, the following: (i) tracking of changes in insulin sensitivity from easily obtainable hear rate data; (ii) individualized assessment of the effects of physical activity; (iii) individualized recommendations for changes in insulin dosing to compensate for the effects of physical activity.

Figure 10:
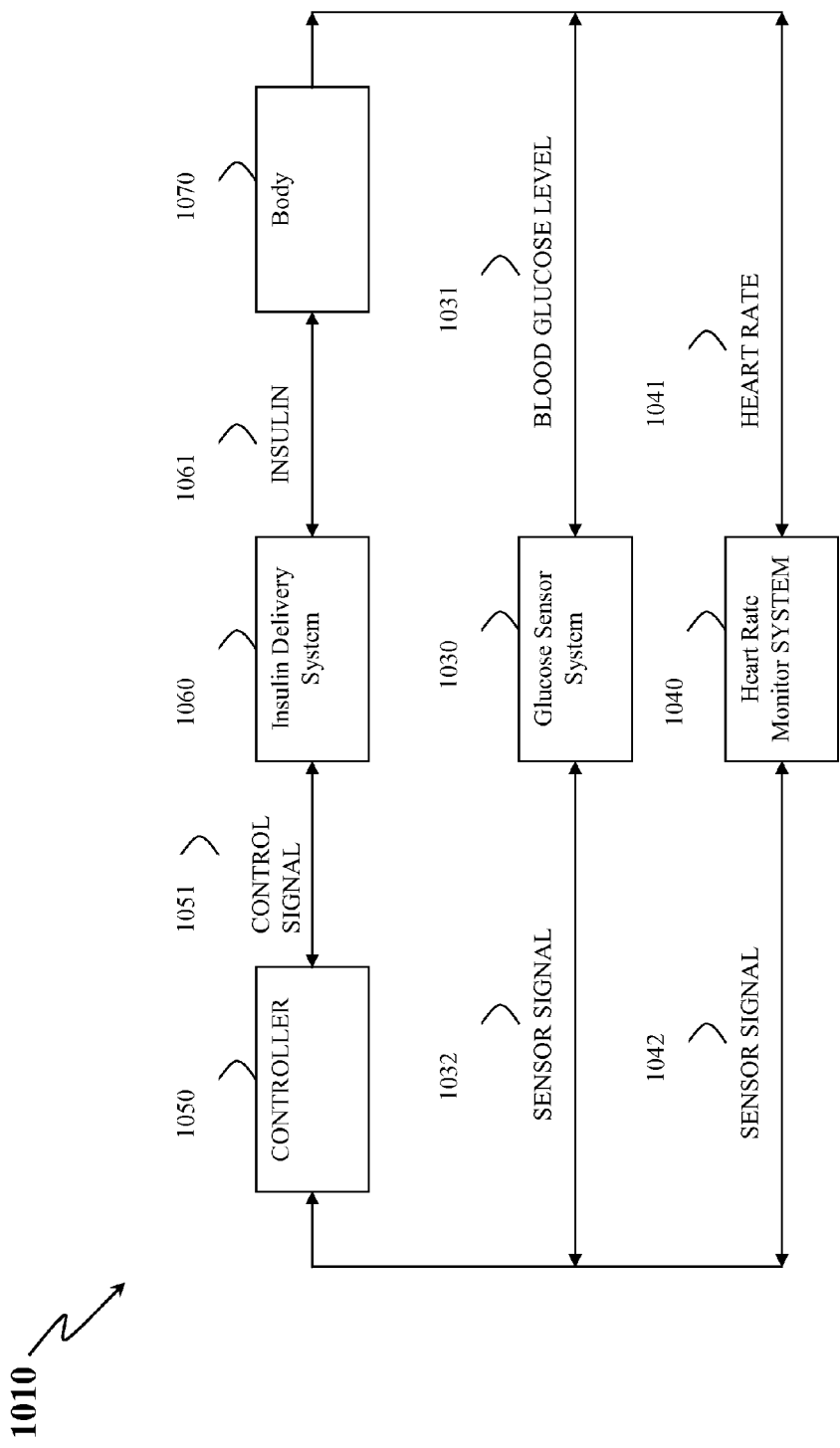
FIG. 10 provides a block diagrammatic representation of one of the embodiments of the invention.

Exemplary Systems:

FIG. 10 shows a block diagrammatic representation of one of the embodiments of the invention. Referring to FIG. 10, there is shown a block diagrammatic representation of the system 1010 comprising a blood glucose sensor system 1030, heart rate monitor 1040, controller 1050, and insulin delivery system 1060. The glucose meter system 1030 is used for reading, inter alia, insulin dosage and blood glucose level 1031 in the body 1070. The glucose sensor system 1030 generates a sensor signal 1032 representative of the blood glucose levels in the body and provides the sensor signal 1032 to the controller 1050. The heart rate monitor system generates a sensor signal 1042 representative of the heart rate of the body 1070 and provides the sensor signal 1042 to the controller 1050. The controller receives the sensor signal 1032 from the glucose sensor system 1030 and sensor signal 1042 from the heart rate monitor system 1040 and generates control signals 1051 that are communicated to the insulin delivery system 1060. The insulin delivery system 1060 receives the control signals 1051 and infuses insulin 1061 into the body 1070 in response to the control signals 1060. The controls signal and/or sensor signals, or any desirable or required signals, may be communicated among or between any of the modules. It should be appreciated that the system 1010 (and the related method and computer product) as shown may include all of the modules as illustrated or any combination of a partial selection of the modules.

The glucose sensor system 1030 may include a glucose sensor, sensor electrical components to provide power to the sensor and generate sensor signal, and a sensor communication system to carry the signal to the controller 1050. The sensor system may be enclosed in a housing separate from the other modules of the system 1010 or may be enclosed in a single housing with the other modules of the system 1010.

The heart rate monitor system 1040 may include a heart rate monitor, monitor electrical components to provide power to the sensor and generate signal 1042, and a communication system to carry the signal 1042 to the controller 1050. The heart rate monitor system 1040 may be enclosed a housing separate from the other modules of the system 1010 or may be enclosed in a single housing with the other modules of the system 1010.

The controller 1050 includes controller electrical components and software to generate control signals for the insulin delivery system 1060. The signals may be sent via wireless or wire means or any combinations thereof. In a particular embodiment, the controller 1050, insulin delivery system 1060, glucose sensor system 1030, and heart rate monitor system 1040 may communicate between or among one another via wire. In further alternative embodiments, the controller 1050, insulin delivery system 1060, glucose sensor system 1030, and heart rate monitor system 1040 may communicate between or among one another via cable, wires, circuitry, electrical traces, blue tooth, fiber optic lines, RF, IR, or ultrasonic transmitters and receivers. The controller may be housed in the infusion device housing or may have its own housing or may be included in a supplemental device.

In an embodiment, the insulin delivery system 1060 includes the infusion device and an infusion tube to infuse insulin into the body 1070. In particular embodiments, the infusion device includes infusion electrical components to activate an infusion motor, an infusion communication system to receive control signals 1051, and an infusion device housing to hold the infusion device.

An example of a glucose sensor system, controller, and insulin pump system is the Paradigm system by Medtronic Minimed or the like. An example of a heart rate monitor include the various types of the Polar Heart Rate Monitors or the like.

The modules of the system 1010 may be separate and singular as shown or may be integral with one another in combination. There may be multiple systems with any combination of the modules shown. Any combination of the modules may exist together in a single housing or in separate housing. Further, any of the modules of the system 1010 and signal means may be duplicated or modified as desired or required for intended use, operation, application or environment.

Figure 11:
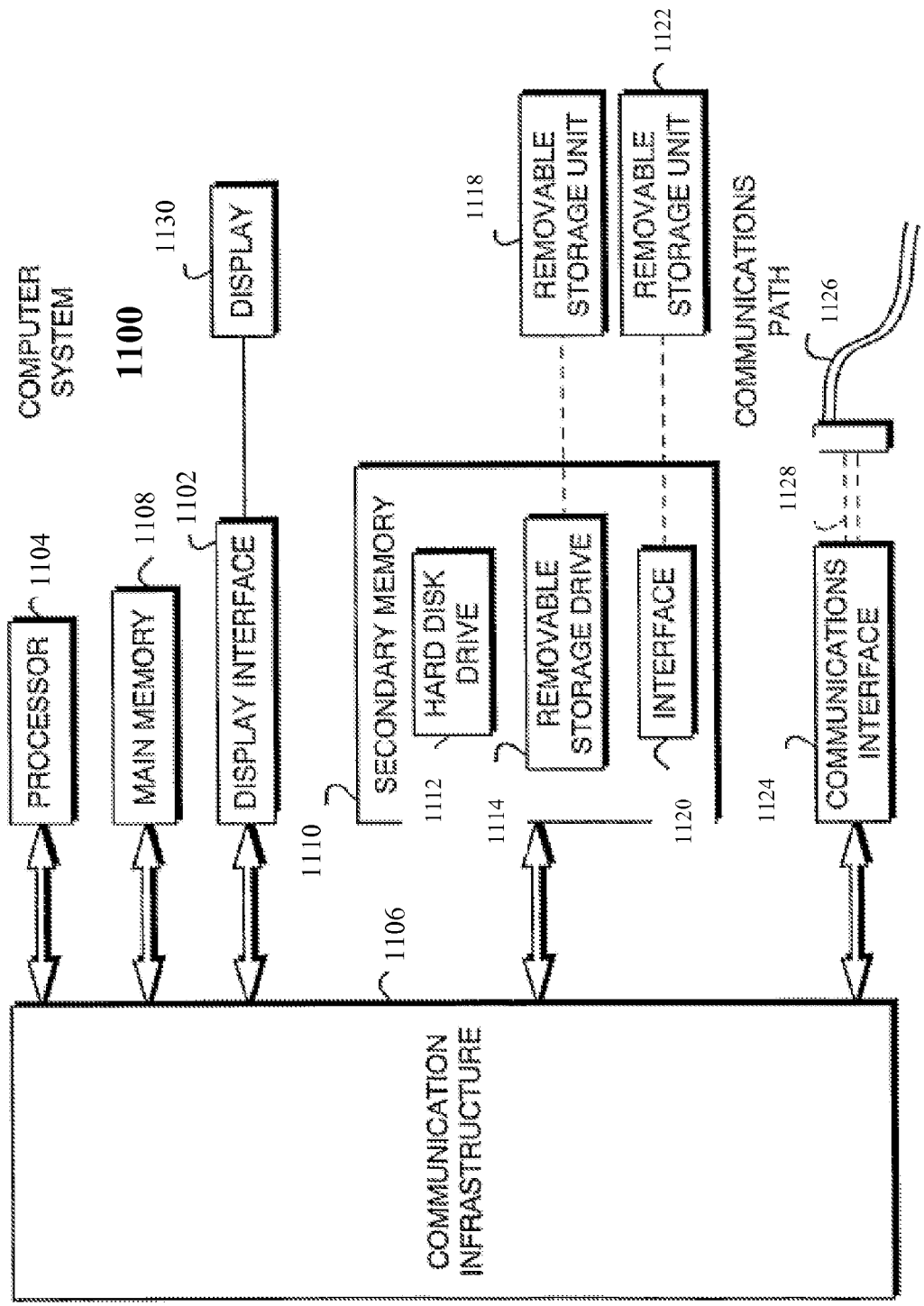
FIG. 11 provides a functional block diagram (an exemplary and non-limiting example) for a computer system for implementation of embodiments of the present invention.

The method of the invention may be implemented using hardware, software or a combination thereof and may be implemented in one or more computer systems or other processing systems, such as a personal digital assistance (PDAs), equipped with adequate memory and processing capabilities. In an example embodiment, the invention may be implemented in software running on a general purpose computer 1100 as illustrated in FIG. 11. Computer system 1100 may include one or more processors, such as processor 1104. Processor 1104 may be connected to a communications infrastructure 1106 (e.g. a communications bus, cross-over bar, or network). Computer system 1100 may include a display interface 1102 that forwards graphics, text, or other data from the communications infrastructure 1106 (or from a frame buffer not shown) for display on the display unit 1130. Display unit 1130 may be digital and/or analog.

Computer system 1100 may also include a main memory 1108, preferably random access memory (RAM), and may also include a secondary memory 1110. The secondary memory 1110 may include, for example, a hard disk drive 1112 and/or a removable storage drive 1114, representing a floppy disk drive, a magnetic tape drive, an optical disk drive, a flash memory, etc. The removable storage drive 1114 reads from and/or writes to a removable storage unit 1118 in a well known manner. Removable storage unit 1118, represents a floppy disk, magnetic tape, optical disc, etc. which is read by and written to by removable storage drive 1114. As will be appreciated, the removable storage unit 1118 may include a computer usable storage medium having stored therein computer software and/or data.

In alternative embodiments, secondary memory 1110 may include other means for allowing computer programs or other instructions to be loaded into computer system 1100. Such means may include, for example, a removable storage unit 1122 and an interface 1120. Examples of such removable storage units/interfaces include a program cartridge and cartridge interface (such as that found in video game devices), a removable memory chip (such as a ROM, PROM, EPROM or EEPROM) and associated socket, and other removable storage units 1122 and interfaces 1120 which allow software and data to be transferred from the removable storage unit 1122 to computer system 1100.

Computer system 1100 may also include a communications interface 1124. Communications interface 1124 allows software and data to be transferred between computer system 1100 and external devices. Examples of communications interface 1124 may include a modem, a network interface (such as an Ethernet card), a communications port (e.g., serial or parallel, etc.), a PCMCIA slot and card, etc. Software and data transferred via communications interface 1124 may be in the form of signals 1128 which may be electronic, electromagnetic, optical or other signals capable of being received by communications interface 1124. Signals 1128 may be provided to communications interface 1124 via a communications path (i.e., channel) 1126. Channel 1126 carries signals 1128 and may be implemented using wire or cable, fiber optics, a phone line, a cellular phone link, an RF link, an infrared link, and other communications channels.

In this document, the terms "computer program medium" and "computer usable medium" are used to generally refer to media such as various software, firmware, disks, drives, removable storage drive 1114, a hard disk installed in hard disk drive 1112, and signals. These computer program products ("computer program medium" and "computer usable medium") are means for providing software to computer systems 1100. The invention includes such computer program products.

Computer programs (also called computer control logic or computer program logic) may be stored in main memory 1108 and/or secondary memory 1110. Computer programs may also be received via communications interface 1124. Such computer programs, when executed, enable computer system 1100 to perform the features of the present invention as discussed herein. In particular, the computer programs, when executed, enable processor 1104 to perform the functions of the present invention. Accordingly, such computer programs represent controllers of computer system 1100. In an embodiment where the invention is implemented using software, the software may be stored in a computer program product and loaded into computer system 1100 using removable storage drive 1114, hard drive 1112 or communications interface 1124. The control logic (software) or computer program logic (software), when executed by the processor 1104, causes the processor 1104 to perform the function of the invention as described herein.

In another embodiment, the invention is implemented primarily in hardware using, for example, hardware components such as application specific integrated circuits (ASICs). Implementation of the hardware state machine to perform the functions described herein will be apparent to persons skilled in the relevant art(s).

In yet another embodiment, the invention is implemented using a combination of both hardware and software.

In an example software embodiment of the invention, the methods described above may be implemented in SPSS control language, but could be implemented in other programs, such as, but not limited to, C++ program language or other programs available to those skilled in the art.

Figure 12:
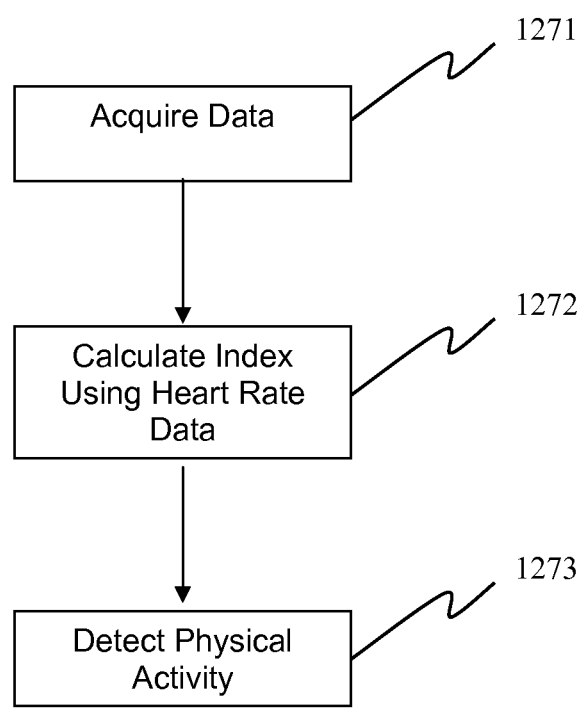
FIG. 12 provides a simplified flowchart of an aspect of an exemplary embodiment of the present invention method, system and computer program product for detecting physical activity, its duration and intensity through HR.

FIG. 12 provides a simplified flowchart of an aspect of an exemplary embodiment of the present invention method, system and computer program product for detecting physical activity, its duration and intensity through HR. Referring to FIG. 12, data is acquired 1271. The data include heart rate data, and may include other data such as glucose data and/or insulin delivery data. Heart rate data may be acquired with, but not limited to, sampling periods less than or equal to 1 minute, sampling periods less than or equal to about 10 minutes, frequently, sampling periods less than or equal to about 15 minutes. Glucose data may be acquired frequently, with a sampling period less than or equal to about 15 minutes, or with other sampling periods. A physical activity index is then calculated 1272 using the acquired heart rate data. Subsequently or concurrently, the index and heart rate data is used to detect physical activity 1273. Physical activity may be detected at, but are not limited to, the completion of acquiring data, near contemporaneously to the latest acquisition data, after the completion of acquiring data, and in real time. It should be appreciated that the aforementioned periods, duration, sequence, timing and/or frequency may be altered as desired or required.

Figure 13:
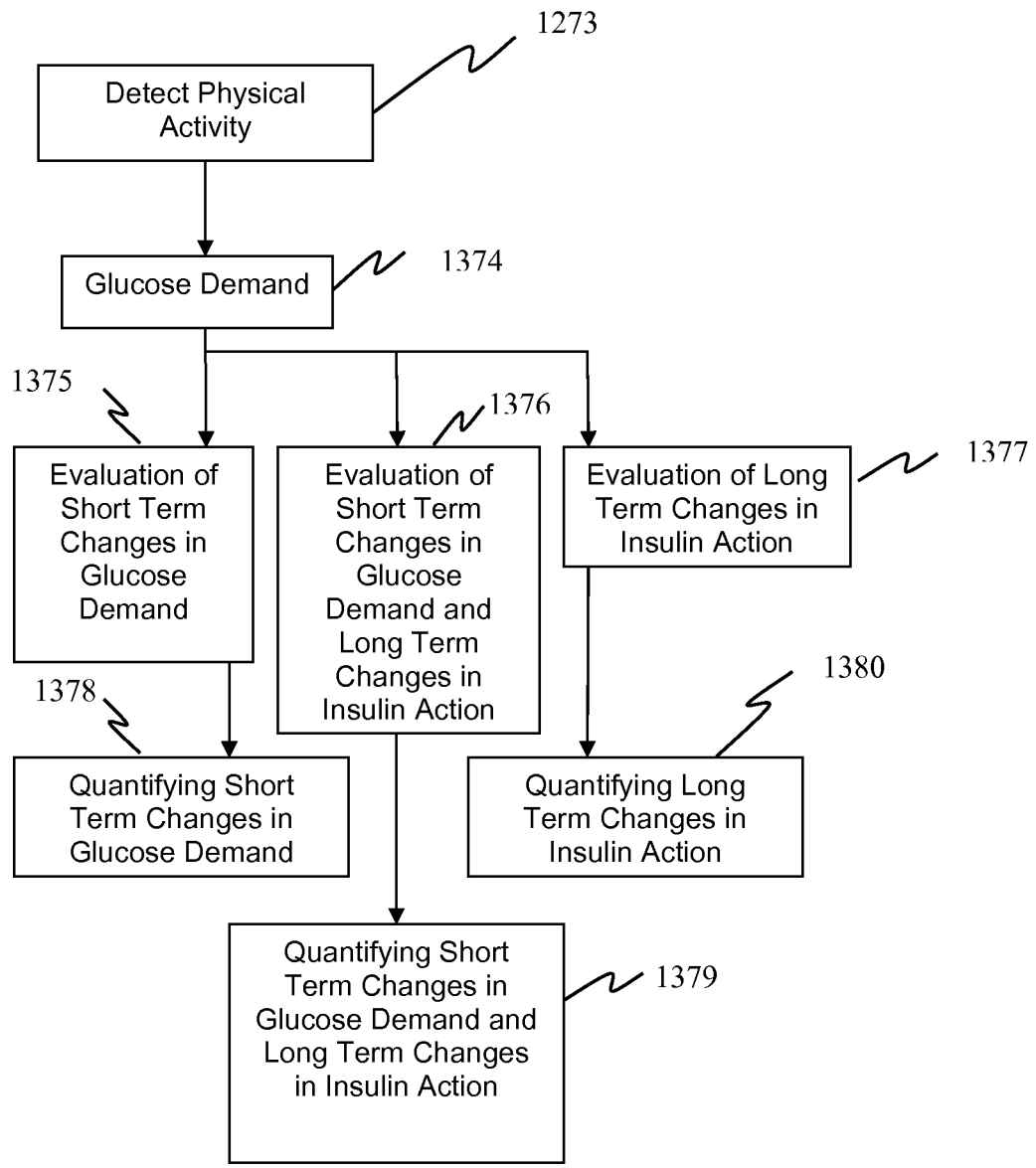
FIG. 13 provides a simplified flowchart of an aspect of an exemplary embodiment of the present invention method, system and computer program product for quantifying short-term and/or long-term changes in insulin sensitivity due to physical activity.

FIG. 13 provides a simplified flowchart of an aspect of an exemplary embodiment of the present invention method, system and computer program product for quantifying short-term and/or long-term changes in insulin sensitivity due to physical activity. Referring to FIG. 13, following the detection of physical activity 1273, the physical activity on glucose demand is evaluated 1374. This may include: evaluating the short term changes in glucose demand 1375, evaluating short term changes in glucose demand and long term changes in insulin action 1376, and/or evaluating the long term changes in insulin action 1377. A short term period may correspond to, but are not limited to, during and within about 15 minutes after physical activity, during and within about 1 hour after physical activity, during and within about 2 hours after physical activity. When evaluating the short term changes in glucose demand, the short term changes in glucose demand is quantified 1378, for example according to Eq. 1.3. When evaluating the long term and short term changes in glucose demand, the long term and short term changes in glucose demand is quantified 1379, for example according to Eq. 1.2. When evaluating the long term changes in glucose demand, the long term changes in insulin action is quantified 1380, for example according to Eq. 1.4. Long term changes correspond to, but are not limited to, at least about 2 hours after physical activity, during and within about 6 hours after physical activity, during and within about 12 hours after physical activity, during and within about 24 hours after physical activity, and during and at least about 24 hours after physical activity. It should be appreciated that the aforementioned periods, duration, sequence, timing and/or frequency may be altered as desired or required. It should be appreciated that alternative solutions of the aforementioned equations may be implemented to achieve the objective of the present invention.

Figure 14:
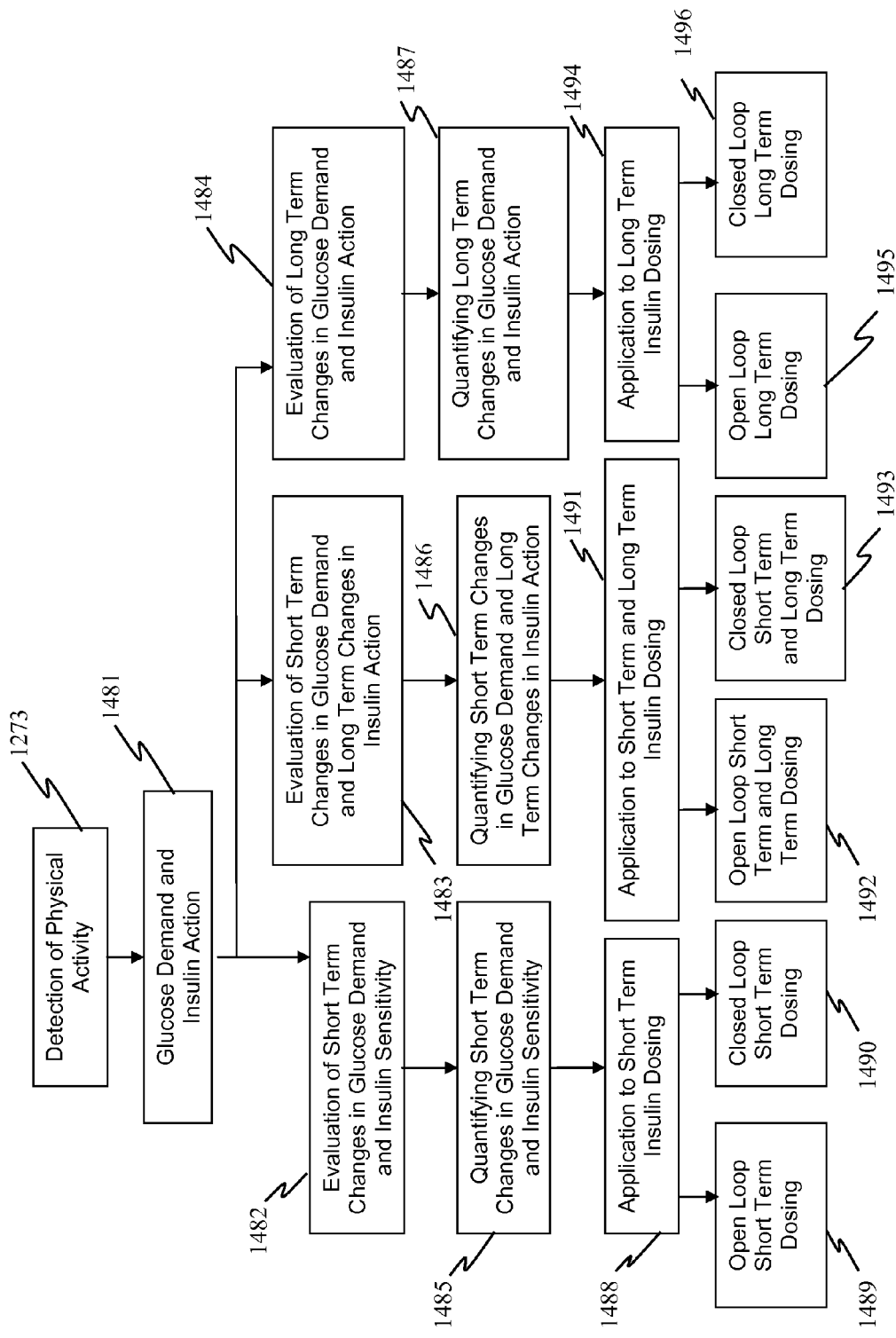
FIG. 14 provides a simplified flowchart of an aspect of an exemplary embodiment of the present invention method, system and computer program product for computing recommended changes in insulin dose to compensate for the effects of physical activity on insulin sensitivity

FIG. 14 provides a simplified flowchart of an aspect of an exemplary embodiment of the present invention method, system and computer program product for computing recommended changes in insulin dose to compensate for the effects of physical activity on insulin sensitivity. Referring to FIG. 14, following the detection of physical activity 1273, the physical activity on glucose demand and insulin action is evaluated 1481. This may include: evaluating the short term changes in glucose demand and insulin sensitivity 1482, evaluating short term changes in glucose demand and long term changes in insulin action 1483, and/or evaluating the long term changes in glucose demand and insulin action 1484. A short term period may correspond to, but are not limited to, during and within about 15 minutes after physical activity, during and within about 1 hour after physical activity, during and within about 2 hours after physical activity. When evaluating the short term changes in glucose demand and insulin sensitivity, the short term changes in glucose demand and insulin sensitivity is quantified 1485, for example according to equation Eq. 1.3. Subsequently, recommendations of insulin dosing 1488 are indicated. In both closed loop 1490 and open loop 1489 applications, basal pump rates and insulin bolus are reduced. In closed loop systems, the injection schedule for short term glucose changes is given by Eq. 3.2. When evaluating the long term and short term changes in glucose demand and insulin sensitivity, the short term changes in glucose demand and long term changes in insulin action is quantified 1486, for example according to Eq. 1.2. Subsequently, recommendations of insulin dosing 1491 are indicated. In both closed loop 1493 and open loop 1492 applications, basal pump rates and insulin bolus are reduced. In closed loop systems, the injection schedule for long term and short term glucose changes is given by Eq. 3.1. When evaluating the long term changes in glucose demand and insulin sensitivity, the long term changes in glucose demand and insulin action is quantified 1487, for example according to Eq. 1.4. Long term changes correspond to, but are not limited to, at least about 2 hours after physical activity, during and within about 6 hours after physical activity, during and within about 12 hours after physical activity, during and within about 24 hours after physical activity, and during and at least about 24 hours after physical activity. Subsequently, recommendations of insulin dosing 1494 are indicated. In both closed loop 1496 and open loop 1495 applications, basal pump rates and insulin bolus are reduced. In closed loop systems, the injection schedule for long term glucose changes is given by Eq. 3.3. It should be appreciated that the aforementioned periods, duration, sequence, timing and/or frequency may be altered as desired or required. It should be appreciated that alternative solutions of the aforementioned equations may be implemented to achieve the objective of the present invention.

It should be appreciated that various aspects of embodiments of the present method, system and computer program product may be implemented with the following methods, systems and computer program products disclosed in the following U.S. patent applications, U.S. patents, and PCT International Patent Applications that are hereby incorporated by reference herein:

1. U.S. Pat. No. 6,572,545 entitled "Method and apparatus for real-time control of physiological parameters;"
2. U.S. Pat. No. 6,399,341 entitled, "Artificial pancreas;"
3. U.S. Pat. No. 6,023,009 entitled, "Artificial pancreas;"
4. U.S. Pat. No. 5,262,055 entitled, "Implantable and refillable biohybrid artificial pancreas;"
5. U.S. Pat. No. 5,116,494 entitled, "Artificial pancreatic perfusion device with temperature sensitive matrix;"
6. U.S. Pat. No. 5,116,493 entitled, "Artificial pancreatic perfusion device with reseedable matrix;"
7. U.S. Pat. No. 5,109,866 entitled, "Artificial pancreas;"
8. U.S. Pat. No. 5,009,230 entitled, "Personal glucose monitor;"
9. U.S. Pat. No. 5,002,661 entitled, "Artificial pancreatic perfusion device;"
10. U.S. Pat. No. 4,936,317 entitled, "Cardiovascular prosthetic devices and implants with porous systems;"
11. U.S. Pat. No. 4,901,728 entitled, "Personal glucose monitor;"
12. U.S. Pat. No. 4,805,624 entitled, "Low-potential electrochemical redox sensors;"
13. U.S. Pat. No. 4,636,144 entitled, "Micro-feed pump for an artificial pancreas;"
14. U.S. Pat. No. 4,627,836 entitled, "Cardiovascular prosthetic devices and implants with porous systems;"
15. U.S. Pat. No. 4,515,584 entitled, "Artificial pancreas;"
16. U.S. Pat. No. 4,459,252 entitled, "Method of forming a small bore flexible vascular graft involving eluting solvent-elutable particles from a polymeric tubular article;"
17. U.S. Pat. No. 4,374,669 entitled, "Cardiovascular prosthetic devices and implants with porous systems;"
18. U.S. Pat. No. 4,355,426 entitled, "Porous flexible vascular graft;"
19. U.S. Pat. No. 4,281,669 entitled, "Pacemaker electrode with porous system;"
20. U.S. Pat. No. 4,242,460 entitled, "Cell culture device;"
21. U.S. Pat. No. 4,242,459 entitled, "Cell culture device;"
22. U.S. Pat. No. 4,053,952 entitled, "Magnetic fluid actuated control valve, relief valve and pump;"

It should be appreciated that various aspects of embodiments of the present method, system and computer program product may be implemented with the following methods, systems and computer program products disclosed in the following U.S. patent applications, U.S. patents, and PCT International patent applications that are hereby incorporated by reference herein and co-owned with the assignee:

PCT International Application Ser. No. PCT/US2005/013792, filed Apr. 21, 2005, entitled "Method, System, and Computer Program Product for Evaluation of the Accuracy of Blood Glucose Monitoring Sensors/Devices;"

U.S. patent application Ser. No. 11/578,831, filed Oct. 18, 2006 entitled "Method, System and Computer Program Product for Evaluating the Accuracy of Blood Glucose Monitoring Sensors/Devices;"

PCT International Application Ser. No. PCT/US01/09884, filed Mar. 29, 2001, entitled "Method, System, and Computer Program Product for Evaluation of Glycemic Control in Diabetes Self-Monitoring Data;"

U.S. Pat. No. 7,025,425 B2 issued Apr. 11, 2006, entitled "Method, System, and Computer Program Product for the Evaluation of Glycemic Control in Diabetes from Self-Monitoring Data;"

U.S. patent application Ser. No. 11/305,946 filed Dec. 19, 2005 entitled "Method, System, and Computer Program Product for the Evaluation of Glycemic Control in Diabetes from Self-Monitoring Data;"

PCT International Application Ser. No. PCT/US2003/025053, filed Aug. 8, 2003, entitled "Method, System, and Computer Program Product for the Processing of Self-Monitoring Blood Glucose (SMBG) Data to Enhance Diabetic Self-Management;"

U.S. patent application Ser. No. 10/524,094 filed Feb. 9, 2005 entitled "Managing and Processing Self-Monitoring Blood Glucose;"

PCT International Application Ser. No PCT/US2006/033724, filed Aug. 29, 2006, entitled "Method for Improvising Accuracy of Continuous Glucose Sensors and a Continuous Glucose Sensor Using the Same;"

PCT International Application No. PCT/US2007/000370, filed Jan. 5, 2007, entitled "Method, System and Computer Program Product for Evaluation of Blood Glucose Variability in Diabetes from Self-Monitoring Data;"

U.S. patent application Ser. No. 11/925,689, filed Oct. 26, 2007, entitled "For Method, System and Computer Program Product for Real-Time Detection of Sensitivity Decline in Analyte Sensors;"

PCT International Application No. PCT/US00/22886, filed Aug. 21, 2000, entitled "Method and Apparatus for Predicting the Risk of Hypoglycemia;"

U.S. Pat. No. 6,923,763 B1, issued Aug. 2, 2005, entitled "Method and Apparatus for Predicting the Risk of Hypoglycemia;"

PCT International Patent Application No. PCT/US2007/082744, filed Oct. 26, 2007, entitled "For Method, System and Computer Program Product for Real-Time Detection of Sensitivity Decline in Analyte Sensors;" and U.S. patent application Ser. No. 11/943,226, filed Nov. 20, 2007, entitled "Systems, Methods, and Computer Program Codes for Recognition of Patterns of Hyperglycemia and Hypoglycemia, Increase Glucose Variability, and Ineffective Self-monitoring in Diabetes."

REFERENCES

The following references are hereby incorporated by reference herein:

[1]. US Senate hearing: The Potential of an Artificial Pancreas: Improving Care for People with Diabetes, Sep. 27, 2006.

[2]. Bergman R N, Ider Y Z, Bowden C R, Cobelli C. Quantitative estimation of insulin sensitivity. Am J Physiol. 236: E667-E677, 1979.

[3]. Bergman R N. The minimal model of glucose regulation: a biography. Advances in Experimental Medicine & Biology 537:1-19, 2003

[4]. Bergman R N. Zaccaro D J. Watanabe R M. Haffner S M. Saad M F. Norris J M. Wagenknecht L E. Hokanson J E. Rotter J I. Rich S S. Minimal model-based insulin sensitivity has greater heritability and a different genetic basis than homeostasis model assessment or fasting insulin. Diabetes 52:2168-74, 2003

[5]. Bergman R N, Finegood D T, Ader M. Assessment of insulin sensitivity in vivo. Am J Physiol 236:E667-677, 1985

[6]. Caumo A. Bergman R N. Cobelli C. Insulin sensitivity from meal tolerance tests in normal subjects: a minimal model index. Journal of Clinical Endocrinology & Metabolism. 85:4396-402, 2000

[7]. Clausen J O. Borch-Johnsen K. Ibsen H. Bergman R N. Hougaard P. Winther K. Pedersen O. Insulin sensitivity index, acute insulin response, and glucose effectiveness in a population-based sample of 380 young healthy Caucasians. Analysis of the impact of gender, body fat, physical fitness, and life-style factors. Journal of Clinical Investigation 98:1195-209, 1996

[8]. Ni T C. Ader M. Bergman R N. Reassessment of glucose effectiveness and insulin sensitivity from minimal model analysis: a theoretical evaluation of the single-compartment glucose distribution assumption. Diabetes 46:1813-21, 1997

[9]. Welch S. Gebhart S S. Bergman R N. Phillips L S. Minimal model analysis of intravenous glucose tolerance test-derived insulin sensitivity in diabetic subjects. Journal of Clinical Endocrinology & Metabolism 71:1508-18, 1990

[10]. Bergman R N, Phillips L S, Cobelli C: Physiologic evaluation of factors controlling glucose tolerance in man: measurement of insulin sensitivity and beta-cell glucose sensitivity from the response to intravenous glucose. J Clin Invest 68:1456-1467, 1981

[11]. Toffolo G, DeGrandi F, Cobelli C: Estimation of β-cell sensitivity from intravenous glucose tolerance tests C-peptide data. Diabetes 44: 845-854, 1995.

[12]. Breda E, Cavaghan M K, Toffolo G, Polonsky K S, and Cobelli C. Oral glucose tolerance test minimal model indexes of beta-cell function and insulin sensitivity. Diabetes 50:150-158, 2001.

[13]. Dalla Man C, Caumo A, and Cobelli C. The oral glucose minimal model: estimation of insulin sensitivity from a meal test. IEEE Trans Biomed Eng 49: 419-429, 2002.

[14]. Dalla Man C, Caumo A, Basu R, Rizza R, Toffolo G, and Cobelli C. Minimal model estimation of glucose absorption and insulin sensitivity from oral test: validation with a tracer method. Am J Physiol Endocrinol Metab 287: E637-E643, 2004.

[15]. Dalla Man C, Yarasheski K E, Caumo A, Robertson H, Toffolo G, Polonsky K S, Cobelli C. Insulin sensitivity by oral glucose minimal models: validation against clamp. Am J Physiol Endocrinol Metab. 289:E954-9, 2005.

[16]. Dalla Man C, Campioni M, Polonsky K S, Basu R, Rizza R A, Toffolo G, Cobelli C. Two-hour seven-sample oral glucose tolerance test and meal protocol: minimal model assessment of beta-cell responsivity and insulin sensitivity in nondiabetic individuals. Diabetes.; 54:3265-73, 2005.

[17]. Basu R, Breda E, Oberg A L, Powell C C, Dalla Man C, Basu A, Vittone J L, Klee G G, Arora P, Jensen M D, Toffolo G, Cobelli C, Rizza R A. Mechanisms of the age-associated deterioration in glucose tolerance: contribution of alterations in insulin secretion, action, and clearance. Diabetes.; 52:1738-48, 2003.

[18]. Callegari T, Caumo A, Cobelli C. Bayesian two-compartment and classic single-compartment minimal models: comparison on insulin modified IVGTT and effect of experiment reduction. IEEE Trans Biomed Eng.; 50:1301-9, 2003.

[19]. Pillonetto G, Sparacino G, Cobelli C. Numerical non-identifiability regions of the minimal model of glucose kinetics: superiority of Bayesian estimation. Math Biosci.; 184:53-67, 2003.

[20]. Dalla Man C, Caumo A, Basu R, Rizza R, Toffolo G, and Cobelli C. Measurement of selective effect of insulin on glucose disposal from labeled glucose oral test minimal model. Am J Physiol Endocrinol Metab 289: E909-E914, 2005

[21]. J F Brun, R Guintrand-Hurget, C Boegner, O Bouix, and A Orsetti. Influence of short-term submaximal exercise on parameters of glucose assimilation analyzed with the minimal model. Metabolism, 44(7):833-840, 1995.

[22]. L J Goodyear, M F Hirshman, and E S Horton. Exercise-induced translocation of skeletal muscle glucose transporters. Am J Physiol, 261:E795-E799, 1991.11

[23]. J Nygren L Jorfeldt J F P Wojtaszewski S D Dufresne E S Horton O Ljungqvist L J Goodyear A Thorell, M F Hirshman. Exercise and insulin cause glut-4 translocation in human skeletal muscle. Am. J. Physiol., 277:E733-E741, 1999.

[24]. E. J. Henriksen. Exercise Effects of Muscle Insulin Signaling and Action: Invited review: Effects of acute exercise and exercise training on insulin resistance. Journal of applied physiology, 93(2):788-796, 2002.

[25]. L Dohm. Exercise effects on muscle insulin signaling and action, invited review: regulation of skeletal muscle glut-4 expression by exercise. J Appl Physiol, 93:782-787, 2002.

[26]. J M Ren, C F Semenkovich, E A Gulve, J Gao, and J O Holloszy. Exercise induces rapid increases in glut4 expression, glucose transport capacity, and insulin-stimulated glycogen storage in muscle. J Bio Chem, 269:14396-14401, 1994.

[27]. L B Borghout and H A Keizer. Exercise and insulin sensitivity: A review. Int J Sports Med, 21:1-12, 2000.

[28]. L J Goodyear and B B Kahn. Exercise, glucose transport, and insulin sensitivity. Annu Rev Med, 49:425-461, 1998.

[29]. Yoichi Hayashi et al. A Single Bout of Exercise at Higher Intensity Enhances Glucose Effectiveness in Sedentary Men. J Clin Endocrinol Metab, 90(7):4035-4040, 2005.

[30]. Y. Nishida et al. Effect of mild exercise training on glucose effectiveness in healthy men. Diabetes Care, 24:1008-1013, 2001.

[31]. Y. Nishida et al. Sg, si, egp of exercise-trained middle-aged men estimated by a two-compartment labelled minimal model Am J Physiol Endocrinol Metab, 283:E809-E816, 2002.

[32]. Y. Nishida et al. Effect of Moderate Exercise Training on Peripheral Glucose Effectiveness, Insulin Sensitivity, and Endogenous Glucose Production in Healthy Humans Estimated by a Two-Compartment-Labeled Minimal Model. Diabetes, 53(2):315-320, 2004.

[33]. S E Kahn et alk. Effect of exercise on insulin action, glucose tolerance, and insulin secretion in aging. Am J Physiol Endocrino Metab, 258:E937-E943, 1990.

[34]. M. Derouich and A. Boutayeb. The effect of physical exercise on the dynamics of glucose and insulin. Journal of Biomechanics, 35:911-917, 2002.

[35]. J Kim, G M Saidel, and M E Cabrera. Multiscale computational model of fuel homeostatsis during exercise. Annals of biomedical Engineering, 35:69-90, 2007.

[36]. M. D. Breton, C. Dalla Man, C. R. King, S. Anderson, L. Farhy, C. Cobelli, and B. P. Kovatchev. Effect of exercise on insulin action assessed by the minimal model. In Proceedings of the Diabetes Technology Meeting, Atlanta Ga., 2006.

[37]. G F Flectcher, G Balady, V F frowlicher, L H Hartley, W L Haskell, and M L Pollock. Exercise standards: A statement for healthcare professionals from the american heart association. Circulation, 91(2):580-615, 1995.

[38]. Weltman, C. J. Pritzlaff, L. Wideman, J. Y. Weltman, J. L. Blumer, R. D. Abbott, M. L. Hartman, and J. D. Veldhuis. Exercise-dependent growth hormone release is linked to markers of heightened central adrenergic outflow. J Appl Physiol, 89(2):629-635, 2000.

[39]. B R Londeree, T R Thomas, G Ziogas, T D Smith, and Q Zhang. V O2max versus HRmax regressions for six modes of exercise. Medecine and Science in Sports and Exercise, 27(3):458-461, 1995.

[40]. Eaton, R. P., R. C. Allen, D. S. Schade, K. M. Erickson, and J. Standefer. Prehepatic insulin production in man: Kinetic analysis using peripheral connecting peptide behaviour. J. Clin. Endocrinol. Metab. 51:520-28, 1980.

[41]. Polonsky, K. S., J. Licinio-Paixao, B. D. Given, W. Pugh, P. Rue, J. Galloway, T. Karrison, and B. Frank. Use of biosynthetic human C-peptide in the measurement of insulin secretion rates in normal volunteers and type I diabetic patients. J. Clin. Invest. 51:98-105, 1986.

[42]. Hovorka, R., E. Koukkou, D. Southerden, J. K. Powrie, M. A. Young. Measuring prehepatic insulin secretion using a population model of C-peptide kinetics: accuracy and required sampling schedule. Diabetologia. 41:548-554, 1998.

[43]. Breda, E., and C. Cobelli. Insulin secretion rate during glucose stimuli: Alternative analyses of C-peptide data. Annals of Biomedical Engineering, 29:692-700, 2001.

[44]. Van Cauter, E., F. Mestrez, J. Sturis, and K. S. Polonsky. Estimation of insulin secretion rates from C-peptide levels. Diabetes. 41:368-377, 1992.

[45]. C. Dalla Man, R. A. Rizza, and C. Cobelli. Meal simulation model of the glucose-insulin system. IEEE Trans Biomed Eng, 2007.

[46]. M Pagani, F Lombardi, S Guzzetti, O Rimoldi, R Furlan, P Pizzinelli, G Sandrone, G Malfatto, S Dell'Orto, and E Piccaluga Power spectral analysis of heart rate and arterial pressure variabilities as a marker of sympatho-vagal interaction in man and conscious dog, Circ. Res.; 59: 178-193, August 1986

[47]. Yamamoto, R. L. Hughson, and J. C. Peterson, Autonomic control of heart rate during exercise studied by heart rate variability spectral analysis, J Appl Physiol 71: 1136-1142, 1991.

In summary, while the present invention has been described with respect to specific embodiments, many modifications, variations, alterations, substitutions, and equivalents will be apparent to those skilled in the art. The present invention is not to be limited in scope by the specific embodiment described herein. Indeed, various modifications of the present invention, in addition to those described herein, will be apparent to those of skill in the art from the foregoing description and accompanying drawings. Accordingly, the invention is to be considered as limited only by the spirit and scope of the following claims, including all modifications and equivalents.

Still other embodiments will become readily apparent to those skilled in this art from reading the above-recited detailed description and drawings of certain exemplary embodiments. It should be understood that numerous variations, modifications, and additional embodiments are possible, and accordingly, all such variations, modifications, and embodiments are to be regarded as being within the spirit and scope of this application. For example, regardless of the content of any portion (e.g., title, field, background, summary, abstract, drawing figure, etc.) of this application, unless clearly specified to the contrary, there is no requirement for the inclusion in any claim herein or of any application claiming priority hereto of any particular described or illustrated activity or element, any particular sequence of such activities, or any particular interrelationship of such elements. Moreover, any activity can be repeated, any activity can be performed by multiple entities, and/or any element can be duplicated. Further, any activity or element can be excluded, the sequence of activities can vary, and/or the interrelationship of elements can vary. Unless clearly specified to the contrary, there is no requirement for any particular described or illustrated activity or element, any particular sequence or such activities, any particular size, speed, material, dimension or frequency, or any particularly interrelationship of such elements. Accordingly, the descriptions and drawings are to be regarded as illustrative in nature, and not as restrictive. Moreover, when any number or range is described herein, unless clearly stated otherwise, that number or range is approximate. When any range is described herein, unless clearly stated otherwise, that range includes all values therein and all sub ranges therein. Any information in any material (e.g., a United States/foreign patent, United States/foreign patent application, book, article, etc.) that has been incorporated by reference herein, is only incorporated by reference to the extent that no conflict exists between such information and the other statements and drawings set forth herein. In the event of such conflict, including a conflict that would render invalid any claim herein or seeking priority hereto, then any such conflicting information in such incorporated by reference material is specifically not incorporated by reference herein.

We claim:

1. A computer-implemented method for detecting physical activity of a patient and its effects on metabolic demand of the metabolic system of said patient, comprising:
   detecting onset of the physical activity using changes in heart rate data of said patient; and
   evaluating effects of physical activity on glucose demand of the metabolic system of said patient, wherein said evaluation is determined by the following steps:
   calculating, by a processor, deviations of heart rate values and blood glucose values from basal heart rate values and basal blood glucose values;
   calculating, by a processor, a quantitative measure of short-term change in glucose demand due to said physical activity; and
   calculating, by a processor, a short term change in glucose demand.

2. The method of claim 1, further comprising:
   acquiring glucose data and heart rate data.

3. The method of claim 2, wherein said detection of physical activity comprising:
   transforming said heart rate data;

computing an index to detect physical activity based on results of said transformation; and detecting physical activity using said index and said heart rate data.

4. The method of claim 3, wherein said index is calculated as:

$$I_{EX} = \frac{\sum_{v>0.15\,Hz} P_t(v)}{\sum_{v\leq 0.15\,Hz} P_t(v)}$$

where $P_t(v)$ is an estimate of a power spectrum of a first order difference of the heart rate signal at time t and frequency v.

5. The method of claim 2, wherein said heart rate data is acquired frequently.

6. The method of claim 2, wherein said heart rate data is acquired with a sampling period less than or equal to about 1 minute.

7. The method of claim 2, wherein said heart rate data is acquired with a sampling period less than or equal to about 10 minutes.

8. The method of claim 2, wherein said glucose data is acquired frequently.

9. The method of claim 2, wherein said glucose data is acquired with a sampling period less than or equal to about 15 minutes.

10. The method of claim 1, wherein said effects are evaluated during and within about 15 minutes after physical activity.

11. The method of claim 1, wherein said effects are evaluated during and within about 1 hour after physical activity.

12. The method of claim 1, wherein said effects are evaluated during and within about 2 hours after physical activity.

13. The method of claim 1, wherein the following equations are used in the calculation of said quantitative measure of short term change in glucose demand as:

$$\begin{cases} \dot{G} = -p_1(G - G_b) - (1 + \beta Y)X \cdot G + \frac{D}{V_g} & (1) \\ \dot{X} = -p_2 X + p_3(I - I_b) & (2) \\ \dot{Y} = -\frac{1}{\tau_{HR}} Y + \frac{1}{\tau_{HR}}(HR - HR_b) & (3) \end{cases}$$

wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity,
β represents the short term metabolic demand to heart rate ratio,
HR represents heart rate,
$HR_b$ represents basal heart rate,
$p_1$ represents the balance between liver production/demand and insulin independent glucose demand,
$\tau_{HR}$ represents the lag between onset of physical activity and changes in metabolic demand,
$p_2$ represents the lag between appearance of insulin and action of insulin, and
$p_3$ represents the intensity of insulin action.

14. The method of claim 1, wherein said evaluation comprises:
calculating deviations of heart rate values and blood glucose values from basal heart rate values and basal blood glucose values;
calculating a quantitative measure of long-term change in glucose demand due to said physical activity; and
calculating a long term change in metabolic demand.

15. The method of claim 14, wherein said effects are evaluated at least about 2 hours after physical activity.

16. The method of claim 14, wherein said effects are evaluated during and within about 6 hours after physical activity.

17. The method of claim 14, wherein said effects are evaluated during and within about 12 hours after physical activity.

18. The method of claim 14, wherein said effects are evaluated during and within about 24 hours after physical activity.

19. The method of claim 14, wherein said effects are evaluated during and at least about 24 hours after physical activity.

20. The method of claim 14, wherein the following equations are used in the calculation of said quantitative measure of long term change in insulin action:

$$\begin{cases} \dot{G} = -p_1(G - G_b) - (1 + \alpha Z)X \cdot G + \frac{D}{V_g} & (1) \\ \dot{X} = -p_2 X + p_3(I - I_b) & (2) \\ \dot{Y} = -\frac{1}{\tau_{HR}} Y + \frac{1}{\tau_{HR}}(HR - HR_b) & (3) \\ \dot{Z} = -\left(f(Y) + \frac{1}{\tau}\right) \cdot Z + f(Y) & (4) \end{cases}$$

$$\text{where } f(Y) = \frac{\left(\frac{Y}{a \cdot HR_b}\right)^n}{1 + \left(\frac{Y}{a \cdot HR_b}\right)^n}$$

wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity,
β represents the short term metabolic demand to heart rate ratio,
Z represents the long-term change in insulin sensitivity due to physical activity,
α represents the long term change amplitude,
HR represents heart rate,
$HR_b$ represents basal heart rate,
$p_1$ represents the balance between liver production/demand and insulin independent glucose demand,
$\tau_{HR}$ represents the lag between onset of physical activity and changes in metabolic demand,
$p_2$ represents the lag between appearance of insulin and action of insulin,
$p_3$ represents the intensity of insulin action,
a represents the fraction of basal heart rate above basal heart rate at which physical activity is detected, and
n represents the steepness of the aforementioned threshold.

21. The method of claim 1, wherein said evaluation comprises:

calculating deviations of heart rate values and blood glucose values from basal heart rate values and basal blood glucose values;
calculating a quantitative measure of short-term change in glucose demand due to said physical activity;
calculating a quantitative measure of long-term change in glucose demand due to said physical activity; and
calculating a change in metabolic demand.

22. The method of claim 21, wherein said effects are evaluated during and within about 15 minutes after physical activity.

23. The method of claim 21, wherein said effects are evaluated during and within about 1 hour after physical activity.

24. The method of claim 21, wherein said effects are evaluated during and within about 2 hour after physical activity.

25. The method of claim 21, wherein said effects are evaluated at least about 2 hours after physical activity.

26. The method of claim 21, wherein said effects are evaluated within about 6 hours after physical activity.

27. The method of claim 21, wherein said effects are evaluated within about 12 hours after physical activity.

28. The method of claim 21, wherein said effects are evaluated within about 24 hours after physical activity.

29. The method of claim 21, wherein said effects are evaluated about at least 24 hours after physical activity.

30. The method of claim 21, wherein the following equations are used in the calculation of said quantitative measure of short-term change and long-term change in glucose demand:

$$\begin{cases} \dot{G} = -p_1(G - G_b) - (1 + \beta Y + \alpha Z)X \cdot G + \dfrac{D}{V_g} & (1) \\ \dot{X} = -p_2 X + p_3(I - I_b) & (2) \\ \dot{Y} = -\dfrac{1}{\tau_{HR}} Y + \dfrac{1}{\tau_{HR}} (HR - HR_b) & (3) \\ \dot{Z} = -\left(f(Y) + \dfrac{1}{\tau}\right) \cdot Z + f(Y) & (4) \end{cases}$$

$$\text{where } f(Y) = \dfrac{\left(\dfrac{Y}{a \cdot HR_b}\right)^n}{1 + \left(\dfrac{Y}{a \cdot HR_b}\right)^n}$$

wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity
β represents the short term metabolic demand to heart rate ratio,
Z represents the long-term change in insulin sensitivity due to physical activity,
α represents the long term change amplitude,
HR represents heart rate,
$HR_b$ represents basal heart rate,
$p_1$ represents the balance between liver production/demand and insulin independent glucose demand,
$\tau_{HR}$ represents the lag between onset of physical activity and changes in metabolic demand,
$p_2$ represents the lag between appearance of insulin and action of insulin,
$p_3$ represents the intensity of insulin action,
a represents the fraction of basal heart rate above basal heart rate at which physical activity is detected,
n represents the steepness of the aforementioned threshold.

31. A computer-implemented method for detecting physical activity of a patient and its effects on metabolic demand of the metabolic system of said patient, comprising:
acquiring glucose data, insulin delivery data and heart rate data;
detecting, by a processor, onset of the physical activity using changes in the heart rate data;
evaluating, by a processor, changes in insulin sensitivity and glucose demand of the metabolic system of said patient due to the physical activity; and
indicating, by a processor, recommendations of insulin dosing.

32. The method of claim 31, wherein said detection of onset of physical activity occurs at the completion of acquiring said heart rate data.

33. The method of claim 31, wherein said detection of onset of physical activity occurs near contemporaneously to the latest acquisition of said heart rate data.

34. The method of claim 31, wherein said detection of onset of physical activity occurs after the completion of acquiring said heart rate data.

35. The method of claim 31, wherein said detection of onset of physical activity occurs in real time.

36. The method of claim 31, wherein said detection of physical activity comprising:
transforming said heart rate data;
computing an index to detect physical activity based on results of said transformation; and
detecting physical activity using said index and said heart rate data.

37. The method of claim 26, wherein said index is calculated as:

$$I_{EX} = \dfrac{\sum\limits_{\nu > 0.15\, Hz} P_t(\nu)}{\sum\limits_{\nu \leq 0.15\, Hz} P_t(\nu)}$$

where $P_t(v)$ is an estimate of the power spectrum of the first order difference of the heart rate signal at time t and frequency v.

38. The method of claim 31, wherein said glucose data is continuous.

39. The method of claim 31, wherein said heart rate data is acquired frequently.

40. The method of claim 31, wherein said heart rate data is acquired with a sampling period less than or equal to 1 minute.

41. The method of claim 31, wherein said heart rate data is acquired with a sampling period less than or equal to about 10 minutes.

42. The method of claim 31, wherein said glucose data is acquired frequently.

43. The method of claim 31, wherein said glucose data is acquired with a sampling period less than or equal to 15 minutes.

44. The method of claim 31, wherein said indicating recommendations of insulin dosing occurs about 24 hours of acquisition of said heart rate data, said insulin delivery data, and said glucose data.

45. The method of claim 31, wherein said indicating recommendations of insulin dosing occurs within about 12 hours of acquiring said heart rate data, said insulin said delivery data, and said glucose data.

46. The method of claim 31, wherein said indicating recommendations of insulin dosing occurs within about 6 hours of acquiring said heart rate data, said insulin delivery data, and said glucose data.

47. The method of claim 31, wherein said indicating recommendations of insulin dosing occurs at the completion of acquiring said heart rate data, said insulin delivery data, and said glucose data.

48. The method of claim 31, wherein said indicating recommendations of insulin dosing occurs near contemporaneously to the latest acquisition of said heart rate data, said insulin delivery data, and said glucose data.

49. The method of claim 31, wherein said indicating recommendations of insulin dosing occurs after the completion of acquiring said heart rate data, said insulin delivery data, and said glucose data.

50. The method of claim 31, wherein said indicating recommendations of insulin dosing occurs in real time.

51. The method of claim 31, wherein said evaluation comprises:
   calculating deviations of heart rate values and blood glucose values from basal heart rate values and basal blood glucose values;
   calculating a quantitative measure of short-term change in glucose demand and insulin sensitivity due to said physical activity; and
   calculating a short term change in metabolic demand.

52. The method of claim 51, wherein said effects are evaluated within about 1 hour after physical activity.

53. The method of claim 51, wherein said effects are evaluated during and within about 15 minutes after physical activity.

54. The method of claim 51, wherein said effects are evaluated within about 2 hours after physical activity.

55. The method of claim 51, wherein the following equations are used in the calculation of said quantitative measure of short-term change in glucose demand and insulin sensitivity:

$$\begin{cases} \dot{G} = -p_1(G - G_b) - (1 + \beta Y)X \cdot G + \dfrac{D}{V_g} & (1) \\ \dot{X} = -p_2 X + p_3(I - I_b) & (2) \\ \dot{Y} = -\dfrac{1}{\tau_{HR}} Y + \dfrac{1}{\tau_{HR}} (HR - HR_b) & (3) \end{cases}$$

wherein
   G represents glucose value,
   $G_b$ is basal glucose value,
   X is insulin dependent action,
   D represents glucose input,
   V is the diffusion volume,
   I is the insulin value,
   $I_b$ represents basal insulin value,
   Y represents the transient variation in metabolic activity
   β represents the short term metabolic demand to heart rate ratio,
   HR represents heart rate,
   $HR_b$ represents basal heart rate,
   $p_1$ represents the balance between liver production/demand and insulin independent glucose demand,
   $\tau_{HR}$ represents the lag between onset of physical activity and changes in metabolic demand,
   $p_2$ represents the lag between appearance of insulin and action of insulin, and
   $p_3$ represents the intensity of insulin action.

56. The method of claim 31, wherein said recommendations of insulin dosing comprising one or more of the following:
   calculating a quantitative measure of short-term changes in glucose demand and insulin sensitivity due to physical activity;
   reducing basal pump rate; and
   reducing insulin bolus.

57. The method of claim 31, wherein said recommendations of insulin dosing comprising one or more of the following:
   calculating quantitative measures of short-term changes in glucose demand and insulin sensitivity;
   adapting a closed loop insulin prescription;
   reducing basal pump rate; and
   reducing insulin bolus.

58. The method of claim 57, wherein said adaptation of closed loop insulin prescription comprises calculating:

$$\tilde{J}(t) = \frac{J(t)}{1 + \beta Y(t)} + \frac{\beta Y(t)}{1 + \beta Y(t)} J_b$$

wherein:
   $\tilde{J}(t)$ is an optimal injection schedule adapted to physical activity at time t,
   J(t) is an optimal injection schedule at time t,
   Y(t) represents the transient variation in metabolic activity
   $J_b$ is injection needed to obtain the plasma concentration $I_b$,
   β represents the short term metabolic demand to heart rate ratio.

59. The method of claim 31, wherein said evaluation comprises:
   calculating deviations of heart rate values and blood glucose values from basal heart rate values and basal blood glucose values;
   calculating a quantitative measure of long-term change in glucose demand and insulin sensitivity due to said physical activity; and
   calculating a long-term change in metabolic demand.

60. The method of claim 59, wherein said effects are evaluated about at least 2 hours after physical activity.

61. The method of claim 59, wherein said effects are evaluated within about 6 hours after physical activity.

62. The method of claim 59, wherein said effects are evaluated within about 12 hours after physical activity.

63. The method of claim 59, wherein said effects are evaluated within about 24 hours after physical activity.

64. The method of claim 59, wherein said effects are evaluated about at least 24 hours after physical activity.

65. The method of claim 59, wherein the following equations are used in the calculation of said quantitative measure of long term change in glucose demand and insulin action:

$$\begin{cases} \dot{G} = -p_1(G - G_b) - (1 + \alpha Z)X \cdot G + \dfrac{D}{V_g} & (1) \\ \dot{X} = -p_2 X + p_3(I - I_b) & (2) \\ \dot{Y} = -\dfrac{1}{\tau_{HR}}Y + \dfrac{1}{\tau_{HR}}(HR - HR_b) & (3) \\ \dot{Z} = -\left(f(Y) + \dfrac{1}{\tau}\right) \cdot Z + f(Y) & (4) \end{cases}$$

$$\text{where } f(Y) = \frac{\left(\frac{Y}{a \cdot HR_b}\right)^n}{1 + \left(\frac{Y}{a \cdot HR_b}\right)^n}$$

wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity
β represents the short term metabolic demand to heart rate ratio,
Z represents the long-term change in insulin sensitivity due to physical activity,
α represents the long term change amplitude,
HR represents heart rate,
$HR_b$ represents basal heart rate,
$p_1$ represents the balance between liver production/demand and insulin independent glucose demand,
$\tau_{HR}$ represents the lag between onset of physical activity and changes in metabolic demand,
$p_2$ represents the lag between appearance of insulin and action of insulin,
$p_3$ represents the intensity of insulin action,
a represents the fraction of basal heart rate above basal heart rate at which physical activity is detected, and
n represents the steepness of the aforementioned threshold.

66. The method of claim 31, wherein said recommendations of insulin dosing comprising one or more of the following:
calculating a quantitative measure of long-term changes in glucose demand and insulin sensitivity due to physical activity;
reducing basal pump rate; and
reducing insulin bolus.

67. The method of claim 31, wherein said recommendations of insulin dosing comprising one or more of the following:
calculating a quantitative measures of long-term changes in glucose demand and insulin sensitivity;
adapting a closed loop insulin prescription;
reducing basal pump rate; and
reducing insulin bolus.

68. The method of claim 67, wherein said adaptation of closed loop insulin prescription comprises calculating:

$$\tilde{J}(t) = \frac{J(t)}{1 + \alpha Z(t)} + \frac{\alpha Z(t)}{1 + \alpha Z(t)} J_b$$

wherein:
$\tilde{J}(t)$ is an optimal injection schedule adapted to physical activity at time t,
J(t) is an optimal injection schedule at time t,
Z(t) is the long-term change in insulin sensitivity due to physical activity at time t,
$J_b$ is injection needed to obtain the plasma concentration $I_b$, and
α is the long term change in amplitude.

69. The method of claim 31, wherein said evaluation comprises:
calculating deviations of heart rate values and blood glucose values from basal heart rate values and basal blood glucose values;
calculating a quantitative measure of short-term change in glucose demand and insulin sensitivity due to said physical activity;
calculating a quantitative measure of long-term change in glucose demand and insulin sensitivity due to said physical activity; and
calculating a change in metabolic demand.

70. The method of claim 69, wherein said effects are evaluated within about 1 hour after physical activity.

71. The method of claim 69, wherein said effects are evaluated during and within about 15 minutes after physical activity.

72. The method of claim 69, wherein said effects are evaluated within about 2 hours after physical activity.

73. The method of claim 69, wherein said effects are evaluated about at least 2 hours after physical activity.

74. The method of claim 69, wherein said effects are evaluated within about 6 hours after physical activity.

75. The method of claim 69, wherein said effects are evaluated within about 12 hours after physical activity.

76. The method of claim 69, wherein said effects are evaluated within about 24 hours after physical activity.

77. The method of claim 69, wherein said effects are evaluated about at least 24 hours after physical activity.

78. The method of claim 69, wherein the following equations are used in the calculation of said quantitative measure of short-term change and said quantitative measure of long-term change in glucose demand and insulin sensitivity:

$$\begin{cases} \dot{G} = -p_1(G - G_b) - (1 + \beta Y + \alpha Z)X \cdot G + \dfrac{D}{V_g} & (1) \\ \dot{X} = -p_2 X + p_3(I - I_b) & (2) \\ \dot{Y} = -\dfrac{1}{\tau_{HR}}Y + \dfrac{1}{\tau_{HR}}(HR - HR_b) & (3) \\ \dot{Z} = -\left(f(Y) + \dfrac{1}{\tau}\right) \cdot Z + f(Y) & (4) \end{cases}$$

$$\text{where } f(Y) = \frac{\left(\frac{Y}{a \cdot HR_b}\right)^n}{1 + \left(\frac{Y}{a \cdot HR_b}\right)^n}$$

wherein
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity β represents the short term metabolic demand to heart rate ratio,
Z represents the long-term change in insulin sensitivity due to physical activity,
α represents the long term change amplitude,
HR represents heart rate,
$HR_b$ represents basal heart rate,
$p_1$ represents the balance between liver production/demand and insulin independent glucose demand,
$\tau_{HR}$ represents the lag between onset of physical activity and changes in metabolic demand,
$p_2$ represents the lag between appearance of insulin and action of insulin,
$p_3$ represents the intensity of insulin action,
a represents the fraction of basal heart rate above basal heart rate at which physical activity is detected, and
n represents the steepness of the aforementioned threshold.

79. The method of claim 31, wherein said recommendations of insulin dosing comprising one or more of the following:
calculating a quantitative measure of said long-term changes and said short-term changes in glucose demand and insulin sensitivity due to physical activity;
reducing basal pump rate; and
reducing insulin bolus.

80. The method of claim 31, wherein said recommendations of insulin dosing comprising one or more of the following:
calculating a quantitative measure of short-term changes and long-term changes in glucose demand and insulin sensitivity;
adapting a closed loop insulin prescription;
reducing basal pump rate; and
reducing insulin bolus.

81. The method of claim 80, wherein said adaptation of closed loop insulin prescription comprises calculating:

$$\tilde{J}(t) = \frac{J(t)}{1+\alpha Z(t)+\beta Y(t)} + \frac{\alpha Z(t)+\beta Y(t)}{1+\alpha Z(t)+\beta Y(t)} J_b$$

wherein
$\tilde{J}(t)$ au optimal injection schedule adapted to physical activity at time t,
J(t) an optimal injection schedule at time t,
Z(t) is the long-term change in insulin sensitivity due to physical activity at time t,
Y(t) r represents the transient variation in metabolic activity at time t
$J_b$ is injection needed to obtain the plasma concentration $I_b$,
β represents the short term metabolic: demand to heart rate ratio, and
α is the long term change in amplitude.

82. A system for detecting physical activity of a patient and its effects on metabolic demand of the metabolic system of said patient, said system comprises:
a processor programmed to:
detect onset of the physical activity of the patient using changes in heart rate data; and
evaluate effects of physical activity on glucose demand of the metabolic system of said patient, wherein said evaluation is determined by the following steps:
calculating deviations of heart rate values and blood glucose values from basal heart rate values and basal blood glucose values;
calculating a quantitative measure of short-term change in glucose demand due to said physical activity; and
calculating a short term change in metabolic demand.

83. The system of claim 82, further comprising:
an acquisition module acquiring glucose data and an acquisition module acquiring heart rate data.

84. The system of claim 83, wherein said detection of physical activity comprising:
transforming said heart rate data; computing an index to detect physical activity based on results of said transformation; and
detecting physical activity using said index and said heart rate data.

85. The system of claim 84, wherein said index is calculated as:

$$I_{EX} = \frac{\sum_{\upsilon > 0.15\, Hz} P_t(\upsilon)}{\sum_{\upsilon \leq 0.15\, Hz} P_t(\upsilon)}$$

where Pt(ν) is an estimate of the power spectrum of the first order difference of the heart rate signal at time t and frequency ν.

86. The system of claim 83, wherein the following equations are used in the calculation of said heart rate data is acquired frequently.

87. The system of claim 83, wherein said heart rate data is acquired with a sampling period less than or equal to about 1 minute.

88. The system of claim 83, wherein said heart rate data is acquired with a sampling period less than or equal to about 10 minutes.

89. The system of claim 83, wherein said glucose data is acquired frequently.

90. The system of claim 83, wherein said glucose data is acquired with a sampling period less than or equal to about 15 minutes.

91. The system of claim 82, wherein said effects are evaluated during and within about 15 minutes after physical activity.

92. The system of claim 82, wherein said effects are evaluated during and within about 1 hour after physical activity.

93. The system of claim 82, wherein said effects are evaluated during and within about 2 hour after physical activity.

94. The system of claim 82, wherein the following equations are used in the calculation of said quantitative measure of short term change in glucose demand:

$$\begin{cases} \dot{G} = -p_1(G-G_b)-(1+\beta Y)X \cdot G + \frac{D}{V_g} & (1) \\ \dot{X} = -p_2 X + p_3(I-I_b) & (2) \\ \dot{Y} = -\frac{1}{\tau_{HR}}Y + \frac{1}{\tau_{HR}}(HR-HR_b) & (3) \end{cases}$$

wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity β represents the short term metabolic demand to heart rate ratio,
HR represents heart rate,
$HR_b$ represents basal heart rate,
$p_1$ represents the balance between liver production/demand and insulin independent glucose demand,
$\tau_{HR}$ represents the lag between onset of physical activity and changes in metabolic demand,
$p_2$ represents the lag between appearance of insulin and action of insulin, and
$p_3$ represents the intensity of insulin action.

95. The system of claim 82, wherein said evaluation comprises:
calculating deviations of heart rate values and blood glucose values from basal heart rate values and basal blood glucose values;
calculating a quantitative measure of long-term change in glucose demand due to said physical activity; and
calculating a long term change in metabolic demand.

96. The system of claim 95, wherein said effects are evaluated at least about 2 hours after physical activity.

97. The system of claim 95, wherein said effects are evaluated during and within about 6 hours after physical activity.

98. The system of claim 95, wherein said effects are evaluated during and within about 12 hours after physical activity.

99. The system of claim 95, wherein said effects are evaluated during and within about 24 hours after physical activity.

100. The system of claim 95, wherein said effects are evaluated during and at least about 24 hours after physical activity.

101. The system of claim 95, wherein the following equations are used in the calculation of said quantitative measure of long term change in insulin action:

$$\begin{cases} \dot{G} = -p_1(G - G_b) - (1 + \alpha Z)X \cdot G + \dfrac{D}{V_g} & (1) \\ \dot{X} = -p_2 X + p_3(I - I_b) & (2) \\ \dot{Y} = -\dfrac{1}{\tau_{HR}}Y + \dfrac{1}{\tau_{HR}}(HR - HR_b) & (3) \\ \dot{Z} = -\left(f(Y) + \dfrac{1}{\tau}\right) \cdot Z + f(Y) & (4) \end{cases}$$

$$\text{where } f(Y) = \dfrac{\left(\dfrac{Y}{a \cdot HR_b}\right)^n}{1 + \left(\dfrac{Y}{a \cdot HR_b}\right)^n}$$

wherein:
G represents glucose value,
$G_b$ is basal glucose value,
X is inulin dependent action,
D represents glucose input,
V is the diffusion volume,
I is the insulin value,
$I_b$ represents basal insulin value,
Y represents the transient variation in metabolic activity
β represents the short term metabolic demand to heart rate ratio,
Z represents the long-term change in insulin sensitivity due to physical activity,
α represents the long term change amplitude,
HR represents heart rate,
$HR_b$ represents basal heart rate,
$p_1$ represents the balance between liver production/demand and insulin independent glucose demand,
$\tau_{HR}$ represents the lag between onset of physical activity and changes in metabolic demand,
$p_2$ represents the lag between appearance of insulin and action of insulin,
$p_3$ represents the intensity of insulin action,
a represents the fraction of basal heart rate above basal heart rate at winch physical activity is detected, and
n represents the steepness of the aforementioned threshold.

102. The system of claim 82, wherein said evaluation comprises:
calculating deviations of heart rate values and blood glucose values from basal heart rate values and basal blood glucose values;
calculating a quantitative measure of short-term change in glucose demand due to said physical activity;
calculating a quantitative measure of long-term change in glucose demand due to said physical activity; and
calculating a change in metabolic demand.

103. The system of claim 102, wherein said effects are evaluated during and within about 15 minutes after physical activity.

104. The system of claim 102, wherein said effects are evaluated during and within about 1 hour after physical activity.

105. The system of claim 102, wherein said effects are evaluated during and within about 2 hour after physical activity.

106. The system of claim 102, wherein said effects are evaluated at least about 2 hours after physical activity.

107. The system of claim 102, wherein said effects are evaluated within about 6 hours after physical activity.

108. The system of claim 102, wherein said effects are evaluated within about 12 hours after physical activity.

109. The system of claim 102, wherein said effects are evaluated within about 24 hours after physical activity.

110. The system of claim 102, wherein said effects are evaluated about at least 24 hours after physical activity.

111. The system of claim 102, wherein the following equations are used in the calculation of said quantitative measure of short-term change and long-term change in glucose demand:

$$\begin{cases} \dot{G} = -p_1(G - G_b) - (1 + \beta Y + \alpha Z)X \cdot G + \dfrac{D}{V_g} & (1) \\ \dot{X} = -p_2 X + p_3(I - I_b) & (2) \\ \dot{Y} = -\dfrac{1}{\tau_{HR}}Y + \dfrac{1}{\tau_{HR}}(HR - HR_b) & (3) \\ \dot{Z} = -\left(f(Y) + \dfrac{1}{\tau}\right) \cdot Z + f(Y) & (4) \end{cases}$$

$$\text{where } f(Y) = \dfrac{\left(\dfrac{Y}{a \cdot HR_b}\right)^n}{1 + \left(\dfrac{Y}{a \cdot HR_b}\right)^n}$$

wherein:
G represents glucose value,
$G_b$ basal glucose value,
X is insulin dependent action,
D represents glucose input,
V is the diffusion volume,
I is the insulin value,
$I_b$ basal, insulin value,
Y represents the transient variation in metabolic activity β represents the short term metabolic demand to heart rate ratio, Z represents the long-term change in insulin sensitivity due to physical activity, α represents the long term change amplitude, HR represents heart rate, $HR_b$ represents basal heart rate, $p_1$ represents the balance between liver production/demand and insulin independent glucose demand, $\tau_{HR}$ represents the lag between onset of physical activity and changes in metabolic demand, $p_2$ represents the lag between appearance of insulin and action of insulin, $p_3$ represents the intensity of insulin action, a represents the fraction of basal heart rate above basal heart rate at which physical activity is detected, n represents the steepness of the aforementioned threshold.

112. A system for detecting physical activity of a patient and its effects on metabolic demand of the metabolic system of said patient, said system comprising:
an acquisition module acquiring glucose data, insulin delivery data and heart rate data;
a processor programmed to:
detect onset of the physical activity using changes in heart rate data;
evaluate changes in insulin sensitivity and glucose demand of the metabolic system of the patient due to the physical activity; and
indicate recommendations of insulin dosing.

113. The system of claim 112, wherein said detection of onset of physical activity occurs at the completion of acquiring said heart rate data.

114. The system of claim 112, wherein said detection of onset of physical activity occurs near contemporaneously to the latest acquisition of said heart rate data.

115. The system of claim 112, wherein said detection of onset of physical activity occurs after the completion of acquiring said heart rate data.

116. The system of claim 112, wherein said detection of onset of physical activity occurs in real time.

117. The system of claim 112, wherein said detection of physical activity comprising:
transforming said heart rate data;
computing an index to detect physical activity based on results of said transformation; and
detecting physical activity using said index and said heart rate data.

118. The system of claim 117, wherein said index is calculated as:

$$I_{EX} = \frac{\sum_{v>0.15\ Hz} P_t(v)}{\sum_{v\leq 0.15\ Hz} P_t(v)}$$

where $P_t(v)$ is an estimate of the power spectrum of the first order difference of the heart rate signal at time t and frequency v.

119. The system of claim 112, wherein said glucose data is continuous.

120. The system of claim 112, wherein said heart rate data is acquired frequently.

121. The system of claim 112, wherein said heart rate data is acquired with a sampling period less than or equal to 1 minute.

122. The system of claim 112, wherein said heart rate data is acquired with a sampling period less than or equal to about 10 minutes.

123. The system of claim 112, wherein said glucose data is acquired frequently.

124. The system of claim 112, wherein said glucose data is acquired with a sampling period less than or equal to 15 minutes.

125. The system of claim 112, wherein said indicating recommendations of insulin dosing occurs about 24 hours of acquisition of said heart rate data, said insulin delivery data, and said glucose data.

126. The system of claim 112, wherein said indicating recommendations of insulin dosing occurs within about 12 hours of acquiring said heart rate data, said insulin said delivery data, and said glucose data.

127. The system of claim 112, wherein said indicating recommendations of insulin dosing occurs within about 6 hours of acquiring said heart rate data, said insulin delivery data, and said glucose data.

128. The system of claim 112, wherein said indicating recommendations of insulin dosing occurs at the completion of acquiring said heart rate data, said insulin delivery data, and said glucose data.

129. The system of claim 112, wherein said indicating recommendations of insulin dosing occurs near contemporaneously to the latest acquisition of said heart rate data, said insulin delivery data, and said glucose data.

130. The system of claim 112, wherein said indicating recommendations of insulin dosing occurs after the completion of acquiring said heart rate data, said insulin delivery data, and said glucose data.

131. The system of claim 112, wherein said indicating recommendations of insulin dosing occurs in real time.

132. The system of claim 112, wherein said evaluation comprises:
calculating deviations of heart rate values and blood glucose values from basal heart rate values and basal blood glucose values;
calculating a quantitative measure of short-term change in glucose demand and insulin sensitivity due to said physical activity; and
calculating a short term change in metabolic demand.

133. The system of claim 132, wherein said effects are evaluated within about 1 hour after physical activity.

134. The system of claim 132, wherein said effects are evaluated during and within about 15 minutes after physical activity.

135. The system of claim 132, wherein said effects are evaluated within about 2 hours after physical activity.

136. The system of claim 132, wherein the following equations are used in the calculation of said quantitative measure of short-term change in glucose demand and insulin sensitivity:

$$\begin{cases} \dot{G} = -p_1(G - G_b) - (1 + \beta Y)X \cdot G + \dfrac{D}{V_g} & (1) \\ \dot{X} = -p_2 X + p_3(I - I_b) & (2) \\ \dot{Y} = -\dfrac{1}{\tau_{HR}}Y + \dfrac{1}{\tau_{HR}}(HR - HR_b) & (3) \end{cases}$$

wherein

G represents glucose value, $G_b$ is basal glucose value,

X is insulin dependent action,

D represents glucose input,
V is the diffusion volume,
I is the insulin value,
$I_b$ represents basal insulin value,
Y represents the transient variation in metabolic activity
β represents the short term metabolic demand to heart rate ratio,
HR represents heart rate,
$HR_b$ represents basal heart rate,
$p_1$ represents the balance between liver production/demand and insulin independent glucose demand,
$\tau_{HR}$ represents the lag between onset of physical activity and changes in metabolic demand,
$p_2$ represents the lag between appearance of insulin and action of insulin, and
$p_3$ represents the intensity of insulin action.

137. The system of claim 112, wherein said recommendations of insulin dosing comprising one or more of the following:
 calculating a quantitative measure of short-term changes in glucose demand and insulin sensitivity due to physical activity;
 reducing basal pump rate; and
 reducing insulin bolus.

138. The system of claim 112, wherein said recommendations of insulin dosing comprising one or more of the following:
 calculating quantitative measures of short-term changes in glucose demand and insulin sensitivity; and
 adapting a closed loop insulin prescription for an insulin delivery system to:
 reduce basal pump rate and reduce insulin bolus.

139. The system of claim 138, wherein said adaptation of closed loop insulin prescription comprises calculating:

$$\tilde{J}(t) = \frac{J(t)}{1+\beta Y(t)} + \frac{\beta Y(t)}{1+\beta Y(t)} J_b$$

wherein:
 $\tilde{J}(t)$ an optimal injection schedule adapted to physical activity at time t,
 J(t) is an optimal injection schedule at time t,
 Y(t) represents the transient variation in metabolic activity
 $J_b$ is injection needed to obtain the plasma concentration $I_b$,
 β represents the short term metabolic demand to heart rate ratio.

140. The system of claim 112, wherein said evaluation comprises:
 calculating deviations of heart rate values and blood glucose values from basal heart rate values and basal blood glucose values;
 calculating a quantitative measure of long-term change in glucose demand and insulin sensitivity due to said physical activity; and
 calculating a long-term change in metabolic demand.

141. The system of claim 140, wherein said effects are evaluated to about at least 2 hours after physical activity.

142. The system of claim 140, wherein said effects are evaluated within about 6 hours after physical activity.

143. The system of claim 140, wherein said effects are evaluated within about 12 hours after physical activity.

144. The system of claim 140, wherein said effects are evaluated within about 24 hours after physical activity.

145. The system of claim 140, wherein said effects are evaluated about at least 24 hours after physical activity.

146. The system of claim 140, wherein the following equations are used in the calculation of said quantitative measure of long term change in glucose demand and insulin action:

$$\begin{cases} \dot{G} = -p_1(G-G_b) - (1+\alpha Z)X \cdot G + \dfrac{D}{V_g} & (1) \\ \dot{X} = -p_2 X + p_3(I-I_b) & (2) \\ \dot{Y} = -\dfrac{1}{\tau_{HR}} Y + \dfrac{1}{\tau_{HR}}(HR-HR_b) & (3) \\ \dot{Z} = -\left(f(Y)+\dfrac{1}{\tau}\right) \cdot Z + f(Y) & (4) \end{cases}$$

$$\text{where } f(Y) = \frac{\left(\dfrac{Y}{a \cdot HR_b}\right)^n}{1+\left(\dfrac{Y}{a \cdot HR_b}\right)^n}$$

wherein:
 G represents glucose value,
 $G_b$ is basal glucose value,
 X is insulin dependent action,
 D represents glucose input,
 V is the diffusion volume,
 I is the insulin value,
 $I_b$ represents basal insulin value,
 Y represents the transient variation in metabolic activity
 β represents the short term metabolic demand to heart rate ratio,
 Z represents the long-term change in insulin sensitivity due to physical activity,
 α represents the long term change amplitude,
 HR represents heart rate,
 $HR_b$ represents basal heart rate,
 $p_1$ represents the balance between liver production demand and insulin independent glucose demand,
 $\tau_{HR}$ represents the lag between onset of physical activity and changes in metabolic demand,
 $p_2$ represents the lag between appearance of insulin and action of insulin,
 $p_3$ represents the intensity of insulin action,
 a represents the fraction of basal heart rate above basal heart rate at which physical activity is detected, and
 n represents the steepness of the aforementioned threshold.

147. The system of claim 112, wherein said recommendations of insulin dosing comprising one or more of the following:
 calculating a quantitative measure of long-term changes in glucose demand and insulin sensitivity due to physical activity;
 reducing basal pump rate; and
 reducing insulin bolus.

148. The system of claim 112, wherein said recommendations of insulin dosing comprising one or more of the following:
 calculating a quantitative measures of long-term changes in glucose demand and insulin sensitivity; and
 adapting a closed loop insulin prescription for an insulin delivery system to:
 reduce basal pump rate and reduce insulin bolus.

149. The system of claim 148, wherein said adaptation of closed loop insulin prescription comprises calculating:

$$\tilde{J}(t) = \frac{J(t)}{1+\alpha Z(t)} + \frac{\alpha Z(t)}{1+\alpha Z(t)} J_b$$

wherein:
  $\tilde{J}(t)$ is an optimal injection schedule adapted to physical activity at time t,
  J(t) is an optimal injection schedule at time t,
  Z(t) is the long-term change in insulin sensitivity due physical activity at time t,
  $J_b$ is injection needed to obtain the plasma concentration $I_b$, and
  α is the to term change in amplitude.

150. The system of claim 112, wherein said evaluation comprises:
  calculating deviations of heart rate values and blood glucose values from basal heart rate values and basal blood glucose values;
  calculating a quantitative measure of short-term change in glucose demand and insulin sensitivity due to said physical activity;
  calculating a quantitative measure of long-term change in glucose demand and insulin sensitivity due to said physical activity; and
  calculating a change in metabolic demand.

151. The system of claim 150, wherein said effects are evaluated within about 1 hour after physical activity.

152. The system of claim 150, wherein said effects are evaluated during and within about 15 minutes after physical activity.

153. The system of claim 150, wherein said effects are evaluated within about 2 hours after physical activity.

154. The system of claim 150, wherein said effects are evaluated about at least 2 hours after physical activity.

155. The system of claim 150, wherein said effects are evaluated within about 6 hours after physical activity.

156. The system of claim 150, wherein said effects are evaluated within about 12 hours after physical activity.

157. The system of claim 150, wherein said effects are evaluated within about 24 hours after physical activity.

158. The system of claim 150, wherein said effects are evaluated about at least 24 hours after physical activity.

159. The system of claim 150, wherein the following equations are used in the calculation of said quantitative measure of short-term change and said quantitative measure of long-term change in glucose demand and insulin sensitivity:

$$\begin{cases} \dot{G} = -p_1(G-G_b) - (1+\beta Y + \alpha Z)X \cdot G + \frac{D}{V_g} & (1) \\ \dot{X} = -p_2 X + p_3(I-I_b) & (2) \\ \dot{Y} = -\frac{1}{\tau_{HR}}Y + \frac{1}{\tau_{HR}}(HR-HR_b) & (3) \\ \dot{Z} = -\left(f(Y) + \frac{1}{\tau}\right) \cdot Z + f(Y) & (4) \end{cases}$$

$$\text{where } f(Y) = \frac{\left(\frac{Y}{a \cdot HR_b}\right)^n}{1+\left(\frac{Y}{a \cdot HR_b}\right)^n}$$

wherein:
  G represents glucose value,
  $G_b$ is basal glucose value,
  X is insulin dependent action,
  D represents glucose input,
  V is the diffusion volume,
  I is the insulin value,
    $I_b$ represents basal insulin value,
    Y represents the transient variation in metabolic activity
    β represents the short term metabolic demand to heart rate ratio,
    Z represents the long-term change in insulin sensitivity due to physical activity,
    α represents the long term change amplitude,
    HR represents heart rate,
    $HR_b$ represents basal heart rate,
    $p_1$ represents the balance between liver production demand and insulin independent glucose demand,
    $\tau_{HR}$ represents the lag between onset of physical activity and changes in metabolic demand
    $p_2$ represents the lag between appearance of insulin and action of insulin,
    $p_3$ represents the intensity of insulin action,
    a represents the fraction of basal heart rate above basal heart rate at which physical activity is detected, and
    n represents the steepness of the aforementioned threshold.

160. The system of claim 112, wherein said recommendations of insulin dosing comprising one or more of the following:
  calculating a quantitative measure of said long-term changes and said short-term changes in glucose demand and insulin sensitivity due to physical activity;
  reducing basal pump rate; and
  reducing insulin bolus.

161. The system of claim 112, wherein said recommendations of insulin dosing comprising one or more of the following:
  calculating a quantitative measures of short-term changes and long-term changes in glucose demand and insulin sensitivity; and
  adapting a closed loop insulin prescription for an insulin delivery system to:
  reduce basal pump rate and reduce insulin bolus.

162. The system of claim 161, wherein said adaptation of closed loop insulin prescription comprises calculating:

$$\tilde{J}(t) = \frac{J(t)}{1+\alpha Z(t) + \beta Y(t)} + \frac{\alpha Z(t) + \beta Y(t)}{1+\alpha Z(t) + \beta Y(t)} J_b$$

wherein:
  $\tilde{J}(t)$ an optimal injection schedule adapted to physical activity at time t,
  J(t) is an optima injection schedule at time t,
  Z(t) is the long-term change in insulin sensitivity due to physical activity at time t,
  Y(t) represents the transient variation in metabolic activity at time t
  $J_b$ injection needed to obtain the plasma concentration $I_b$,
  β represents the short term metabolic demand to heart rate ratio, and
  α is the long term change in amplitude.

163. A computer program product comprising a non-transitory computer readable medium having computer executable instructions for detecting physical activity of a patient and its effects on metabolic demand of the metabolic system of said patient, said computer executable instructions comprising instructions for:

detecting onset of the physical activity using changes in heart rate data;

evaluating effects of physical activity on glucose demand of the metabolic system of the patient, wherein said evaluation is determined by the following steps:

calculating deviations of heart rate values and blood glucose values from basal heart rate values and basal blood glucose values;

calculating a quantitative measure of short-term change in glucose demand due to said physical activity; and calculating a short term change in glucose demand.

164. The computer program product of claim 163, further comprising:

acquiring glucose data and heart rate data.

165. The computer program product of claim 164, wherein said detection of physical activity comprising:

transforming said heart rate data;

computing an index to detect physical activity based on results of said transformation; and detecting physical activity using said index and said heart rate data.

166. The computer program product of claim 165, wherein said index is calculated as:

$$I_{EX} = \frac{\sum_{v>0.15\ Hz} P_t(v)}{\sum_{v\leq 0.15\ Hz} P_t(v)}$$

where $P_t(v)$ is an estimate of the power spectrum of the first order difference of the heart rate signal at time t and frequency v.

167. The computer program product of claim 164, wherein said heart rate data is acquired frequently.

168. The computer program product of claim 164, wherein said heart rate data is acquired with a sampling period less than or equal to about 1 minute.

169. The computer program product of claim 164, wherein said heart rate data is acquired with a sampling period less than or equal to about 10 minutes.

170. The computer program product of claim 164, wherein said glucose data is acquired frequently.

171. The computer program product of claim 164, wherein said glucose data is acquired with a sampling period less than or equal to about 15 minutes.

172. The computer program product of claim 163, wherein said effects are evaluated during and within about 15 minutes after physical activity.

173. The computer program product of claim 163, wherein said effects are evaluated during and within about 1 hour after physical activity.

174. The computer program product of claim 163, wherein said effects are evaluated during and within about 2 hours after physical activity.

175. The computer program product of claim 163, wherein the following equations are used in the calculation of said quantitative measure of short term change in glucose demand:

$$\begin{cases} \dot{G} = -p_1(G - G_b) - (1 + \beta Y)X \cdot G + \frac{D}{V_g} & (1) \\ \dot{X} = -p_2 X + p_3(I - I_b) & (2) \\ \dot{Y} = -\frac{1}{\tau_{HR}}Y + \frac{1}{\tau_{HR}}(HR - HR_b) & (3) \end{cases}$$

wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity
β represents the short term metabolic demand to heart rate ratio,
HR represents heart rate,
$HR_b$ represents basal heart rate,
$p_1$ represents the balance between liver production demand and insulin independent glucose demand,
$\tau_{HR}$ represents the lag between onset of physical activity and changes in metabolic demand,
$p_2$ represents the lag between appearance of insulin and action of insulin,
$p_3$ represents the intensity of insulin action.

176. The computer program product of claim 163, wherein said evaluation comprises:

calculating deviations of heart rate values and blood glucose values from basal heart rate values and basal blood glucose values;

calculating a quantitative measure of long-term change in glucose demand due to said physical activity; and calculating a long term change in metabolic demand.

177. The computer program product of claim 176, wherein said effects are evaluated at least about 2 hours after physical activity.

178. The computer program product of claim 176, wherein said effects are evaluated during and within about 6 hours after physical activity.

179. The computer program product of claim 176, wherein said effects are evaluated during and within about 12 hours after physical activity.

180. The computer program product of claim 176, wherein said effects are evaluated during and within about 24 hours after physical activity.

181. The computer program product of claim 176, wherein said effects are evaluated during and at least about 24 hours after physical activity.

182. The computer program product of claim 176, wherein the following equations are used in the calculation of said quantitative measure of long term change in insulin action:

$$\begin{cases} \dot{G} = -p_1(G - G_b) - (1 + \alpha Z)X \cdot G + \frac{D}{V_g} & (1) \\ \dot{X} = -p_2 X + p_3(I - I_b) & (2) \\ \dot{Y} = -\frac{1}{\tau_{HR}}Y + \frac{1}{\tau_{HR}}(HR - HR_b) & (3) \\ \dot{Z} = -\left(f(Y) + \frac{1}{\tau}\right) \cdot Z + f(Y) & (4) \end{cases}$$

-continued $$where\ f(Y) = \frac{\left(\frac{Y}{a \cdot HR_b}\right)^n}{1+\left(\frac{Y}{a \cdot HR_b}\right)^n}$$

wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity
β represents the short term metabolic demand to heart rate ratio,
Z represents the long-term change in insulin sensitivity due to physical activity,
α represents the long term change amplitude,
HR represents heart rate,
$HR_b$ represents basal heart rate,
  $p_1$ represents the balance between liver production demand and insulin independent glucose demand,
  $\tau_{HR}$ represents the lag between onset of physical activity and changes in metabolic demand,
  $p_2$ represents the lag between appearance of insulin and action of insulin,
  $p_3$ represents the intensity of insulin action,
  a represents the fraction of basal heart rate above basal heart rate at which physical activity is detected, and
  n represents the steepness of the aforementioned threshold.

183. The computer program product of claim 163, wherein said evaluation comprises:
  calculating deviations of heart rate values and blood glucose values from basal heart rate values and basal blood glucose values;
  calculating a quantitative measure of short-term change in glucose demand due to said physical activity; calculating a quantitative measure of long-term change in glucose demand due to said physical activity; and
  calculating a change in metabolic demand.

184. The computer program product of claim 183, wherein said effects are evaluated during and within about 15 minutes after physical activity.

185. The computer program product of claim 183, wherein said effects are evaluated during and within about 1 hour after physical activity.

186. The computer program product of claim 183, wherein said effects are evaluated during and within about 2 hours after physical activity.

187. The computer program product of claim 183, wherein said effects are evaluated at least about 2 hours after physical activity.

188. The computer program product of claim 183, wherein said effects are evaluated within about 6 hours after physical activity.

189. The computer program product of claim 183, wherein said effects are evaluated within about 12 hours after physical activity.

190. The computer program product of claim 183, wherein said effects are evaluated within about 24 hours after physical activity.

191. The computer program product of claim 183, wherein said effects are evaluated about at least 24 hours after physical activity.

192. The computer program product of claim 183, wherein the following equations are used in the calculation of said quantitative measure of short-term change and long-term change in glucose demand:

$$\begin{cases} \dot{G} = -p_1(G-G_b) - (1+\beta Y + \alpha Z)X \cdot G + \frac{D}{V_g} & (1) \\ \dot{X} = -p_2 X + p_3(I-I_b) & (2) \\ \dot{Y} = -\frac{1}{\tau_{HR}}Y + \frac{1}{\tau_{HR}}(HR-HR_b) & (3) \\ \dot{Z} = -\left(f(Y)+\frac{1}{\tau}\right)\cdot Z + f(Y) & (4) \end{cases}$$

$$where\ f(Y) = \frac{\left(\frac{Y}{a \cdot HR_b}\right)^n}{1+\left(\frac{Y}{a \cdot HR_b}\right)^n}$$

wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity
β represents the short term metabolic demand to heart rate ratio,
Z represents the long-term change in insulin sensitivity due to physical activity,
α represents the long term change amplitude,
HR represents heart rate,
$HR_b$ represents basal heart rate,
  $p_1$ represents the balance between liver production demand and insulin independent glucose demand,
  $\tau_{HR}$ represents the lag between onset of physical activity and changes in metabolic demand,
  $p_2$ represents the lag between appearance of insulin and action of insulin,
  $p_3$ represents the intensity of insulin action,
  a represents the fraction of basal heart rate above basal heart rate at which physical activity is detected,
  n represents the steepness of the aforementioned threshold.

193. A computer program product comprising a non-transitory computer readable medium having computer executable instructions for detecting physical activity and its effects on metabolic demand, said computer executable instructions comprising instructions for:
  acquiring glucose data, insulin delivery data and heart rate data;
  detecting onset of the physical activity using changes in heart rate data;
  evaluating changes in insulin sensitivity and glucose demand due to the physical activity; and
  indicating recommendations of insulin dosing.

194. The computer program product of claim 193, wherein said detection of onset of physical activity occurs at the completion of acquiring said heart rate data.

195. The computer program product of claim 193, wherein said detection of onset of physical activity occurs near contemporaneously to the latest acquisition of said heart rate data.

196. The computer program product of claim 193, wherein said detection of onset of physical activity occurs after the completion of acquiring said heart rate data.

197. The computer program product of claim 193, wherein said detection of onset of physical activity occurs in real time.

198. The computer program product of claim 193, wherein said detection of physical activity comprising:
  transforming said heart rate data;
  computing an index to detect physical activity based on results of said transformation; and
  detecting physical activity using said index and said heart rate data.

199. The computer program product of claim 198, wherein said index is calculated as:

$$I_{EX} = \frac{\sum_{\nu>0.15\,Hz} P_t(\nu)}{\sum_{\nu\leq 0.15\,Hz} P_t(\nu)}$$

where $P_t(\nu)$ is an estimate of a power spectrum of a first order difference of the heart rate signal at time t and frequency $\nu$.

200. The computer program product of claim 193, wherein said glucose data is continuous.

201. The computer program product of claim 193, wherein said heart rate data is acquired frequently.

202. The computer program product of claim 193, wherein said heart rate data is acquired with a sampling period less than or equal to 1 minute.

203. The computer program product of claim 193, wherein said heart rate data is acquired with a sampling period less than or equal to about 10 minutes.

204. The computer program product of claim 193, wherein said glucose data is acquired frequently.

205. The computer program product of claim 193, wherein said glucose data is acquired with a sampling period less than or equal to 15 minutes.

206. The computer program product of claim 193, wherein said indicating recommendations of insulin dosing occurs about 24 hours of acquisition of said heart rate data, said insulin delivery data, and said glucose data.

207. The computer program product of claim 193, wherein said indicating recommendations of insulin dosing occurs within about 12 hours of acquiring said heart rate data, said insulin said delivery data, and said glucose data.

208. The computer program product of claim 193, wherein said indicating recommendations insulin dosing occurs within about 6 hours of acquiring said heart rate data, said insulin delivery data, and said glucose data.

209. The computer program product of claim 193, wherein said indicating recommendations of insulin dosing occurs at the completion of acquiring said heart rate data, said insulin delivery data, and said glucose data.

210. The computer program product of claim 193, wherein said indicating recommendations of insulin dosing occurs near contemporaneously to the latest acquisition of said heart rate data, said insulin delivery data, and said glucose data.

211. The computer program product of claim 193, wherein said indicating recommendations of insulin dosing occurs after the completion of acquiring said heart rate data, said insulin delivery data, and said glucose data.

212. The computer program product of claim 193, wherein said indicating recommendations of insulin dosing occurs in real time.

213. The computer program product of claim 193, wherein said evaluation comprises:
  calculating deviations of heart rate values and blood glucose values from basal heart rate values and basal blood glucose values;
  calculating a quantitative measure of short-term change in glucose demand and insulin sensitivity due to said physical activity; and
  calculating a short term change in metabolic demand.

214. The computer program product of claim 213, wherein said effects are evaluated within about 1 hour after physical activity.

215. The computer program product of claim 213, wherein said effects are evaluated during and within about 15 minutes after physical activity.

216. The computer program product of claim 213, wherein said effects are evaluated within about 2 hours after physical activity.

217. The computer program product of claim 213, wherein the following equations are used in the calculation of said quantitative measure of short-term change in glucose demand and insulin sensitivity:

$$\begin{cases} \dot{G} = -p_1(G - G_b) - (1 + \beta Y)X \cdot G + \dfrac{D}{V_g} & (1) \\ \dot{X} = -p_2 X + p_3(I - I_b) & (2) \\ \dot{Y} = -\dfrac{1}{\tau_{HR}} Y + \dfrac{1}{\tau_{HR}}(HR - HR_b) & (3) \end{cases}$$

wherein
  G represents glucose value,
  $G_b$ is basal glucose value,
  X is insulin dependent action,
  D represents glucose input,
  V is the diffusion volume,
  I is the insulin value,
  $I_b$ represents basal insulin value,
  Y represents the transient variation in metabolic activity
  β represents the short term metabolic demand to heart rate ratio,
  HR represents heart rate,
  $HR_b$ represents basal heart rate,
  $p_1$ represents the balance between liver production demand and insulin independent glucose demand,
  $\tau_{HR}$ represents the lag between onset of physical activity and changes in metabolic demand,
  $p_2$ represents the lag between appearance of insulin and action of insulin,
  $p_3$ represents the intensity of insulin action.

218. The computer program product of claim 193, wherein said recommendations of insulin dosing comprising one or more of the following:
  calculating a quantitative measure of short-term changes in glucose demand and insulin sensitivity due to physical activity;
  reducing basal pump rate; and
  reducing insulin bolus.

219. The computer program product of claim 193, wherein said recommendations of insulin dosing comprising one or more of the following:
  calculating quantitative measures of short-term changes in glucose demand and insulin sensitivity;

adapting a closed loop insulin prescription;
reducing basal pump rate; and
reducing insulin bolus.

220. The computer program product of claim 219, wherein said adaptation of closed loop insulin prescription comprises calculating:

$$\tilde{J}(t) = \frac{J(t)}{1+\beta Y(t)} + \frac{\beta Y(t)}{1+\beta Y(t)} J_b$$

wherein:
$\tilde{J}(t)$ is an optimal injection schedule adapted to at time t,
J(t) is an optimal injection schedule at time t,
Y(t) represents the transient variation in metabolic activity
$J_b$ injection needed to obtain the plasma concentration $I_b$,
β represents the short term metabolic demand to heart rate ratio.

221. The computer program product of claim 193, wherein said evaluation comprising:
calculating deviations of heart rate values and blood glucose values from basal heart rate values and basal blood glucose values;
calculating a quantitative measure of long-term change in glucose demand and insulin sensitivity due to said physical activity; and
calculating a long-term change in metabolic demand.

222. The computer program product of claim 221, wherein said effects are evaluated about at least 2 hours after physical activity.

223. The computer program product of claim 221, wherein said effects are evaluated within about 6 hours after physical activity.

224. The computer program product of claim 221, wherein said effects are evaluated within about 12 hours after physical activity.

225. The computer program product of claim 221, wherein said effects are evaluated within about 24 hours after physical activity.

226. The computer program product of claim 221, wherein said effects are evaluated about at least 24 hours after physical activity.

227. The computer program product of claim 221, wherein the following equations are used in the calculation of said quantitative measure of long term change in glucose demand and insulin action:

$$\begin{cases} \dot{G} = -p_1(G-G_b) - (1+\alpha Z)X \cdot G + \frac{D}{V_g} & (1) \\ \dot{X} = -p_2 X + p_3(I - I_b) & (2) \\ \dot{Y} = -\frac{1}{\tau_{HR}}Y + \frac{1}{\tau_{HR}}(HR - HR_b) & (3) \\ \dot{Z} = -\left(f(Y) + \frac{1}{\tau}\right) \cdot Z + f(Y) & (4) \end{cases}$$

$$\text{where } f(Y) = \frac{\left(\frac{Y}{a \cdot HR_b}\right)^n}{1 + \left(\frac{Y}{a \cdot HR_b}\right)^n}$$

wherein:
G represents glucose value,
$G_b$ is basal glucose value,
X is insulin dependent action,
D represents glucose input,
V is the diffusion volume,
I is the insulin value,
Y represents the transient variation in metabolic activity
β represents the short term metabolic demand to heart rate ratio,
Z represents the long-term change in insulin sensitivity due to physical activity,
α represents the long term change amplitude,
HR represents heart rate,
$HR_b$ represents basal heart rate,
$p_1$ represents the balance between liver production demand and insulin independent glucose demand,
$\tau_{HR}$ represents the lag between onset of physical activity and changes in metabolic demand,
$p_2$ represents the lag between appearance of insulin and action of insulin,
$p_3$ represents the intensity of insulin action,
a represents the fraction of basal heart rate above basal heart rate at which physical activity is detected, and
n represents the steepness of the aforementioned threshold.

228. The computer program product of claim 193, wherein said recommendations of insulin dosing comprising one or more of the following:
calculating a quantitative measure of long-term changes in glucose demand and insulin sensitivity due to physical activity;
reducing basal pump rate; and
reducing insulin bolus.

229. The computer program product of claim 193, wherein said recommendations of insulin dosing comprising one or more of the following:
calculating a quantitative measures of long-term changes in glucose demand and insulin sensitivity;
adapting a closed loop insulin prescription;
reducing basal pump rate; and
reducing insulin bolus.

230. The computer program product of claim 229, wherein said adaptation of closed loop insulin prescription comprises calculating:

$$\tilde{J}(t) = \frac{J(t)}{1+\alpha Z(t)} + \frac{\alpha Z(t)}{1+\alpha Z(t)} J_b$$

wherein:
$\tilde{J}(t)$ is an optimal injection schedule adapted to physical activity at time t,
J(t) is an optimal injection schedule at time t,
Z(t) is the long-term change in insulin sensitivity due to physical activity a time t,
$J_b$ is injection needed to obtain the plasma concentration $I_b$, and
α is the term change in amplitude.

231. The computer program product of claim 193, wherein said evaluation comprising:
calculating deviations of heart rate values and blood glucose values from basal heart rate values and basal blood glucose values;
calculating a quantitative measure of short-term change in glucose demand and insulin sensitivity due to said physical activity;
calculating a quantitative measure of long-term change in glucose demand and insulin sensitivity due to said physical activity; and calculating a change in metabolic demand.

232. The computer program product of claim 231, wherein said short term effects correspond to within about 1 hour after physical activity.

233. The computer program product of claim 231, wherein said short term effects correspond to during and within about 15 minutes after physical activity.

234. The computer program product of claim 231, wherein said short term effects correspond to within about 2 hours after physical activity.

235. The computer program product of claim 231, wherein said effects are evaluated about at least 2 hours after physical activity.

236. The computer program product of claim 231, wherein said effects are evaluated within about 6 hours after physical activity.

237. The computer program product of claim 231, wherein said effects are evaluated within about 12 hours after physical activity.

238. The computer program product of claim 231, wherein said effects are evaluated within about 24 hours after physical activity.

239. The computer program product of claim 231, wherein said effects are evaluated about at least 24 hours after physical activity.

240. The computer program product of claim 231, wherein the following equations are used in the calculation of said quantitative measure of short-term change and said quantitative measure of long-term change in glucose demand and insulin sensitivity:

$$\begin{cases} \dot{G} = -p_1(G - G_b) - (1 + \beta Y + \alpha Z)X \cdot G + \dfrac{D}{V_g} & (1) \\ \dot{X} = -p_2 X + p_3(I - I_b) & (2) \\ \dot{Y} = -\dfrac{1}{\tau_{HR}} Y + \dfrac{1}{\tau_{HR}}(HR - HR_b) & (3) \\ \dot{Z} = -\left(f(Y) + \dfrac{1}{\tau}\right) \cdot Z + f(Y) & (4) \end{cases}$$

where $f(Y) = \dfrac{\left(\dfrac{Y}{a \cdot HR_b}\right)^n}{1 + \left(\dfrac{Y}{a \cdot HR_b}\right)^n}$ wherein:
G represents glucose value,
$G_b$ is basal glucose value,
X is insulin dependent action,
D represents glucose input,
V is the diffusion volume,
I is the insulin value,
$I_b$ represents basal insulin value,
Y represents the transient variation in metabolic activity
β represents the short term metabolic demand to heart rate ratio,
Z represents the long-term change in insulin sensitivity due to physical activity,
α represents the long term change amplitude,
HR represents heart rate,
$HR_b$ represents basal heart rate,
$p_1$ represents the balance between liver production demand and insulin independent glucose demand,
$\tau_{HR}$ represents the lag between onset of physical activity and changes in metabolic demand,
$p_2$ represents the lag between appearance of insulin and action of insulin,
$p_3$ represents the intensity of insulin action,
a represents the fraction of basal heart rate above basal heart rate at which physical activity is detected, and
n represents the steepness of the aforementioned threshold.

241. The computer program product of claim 193, wherein said recommendations of insulin dosing comprising one or more of the following:
calculating a quantitative measure of said long-term changes and said short-term changes in glucose demand and insulin sensitivity due to physical activity;
reducing basal pump rate; and
reducing insulin bolus.

242. The computer program product of claim 193, wherein said recommendations of insulin dosing comprising one or more of the following:
calculating a quantitative measures of short-term changes and long-term changes in glucose demand and insulin sensitivity;
adapting a closed loop insulin prescription;
reducing basal pump rate; and
reducing insulin bolus.

243. The computer program product of claim 242, wherein said adaptation of closed loop insulin prescription comprises calculating:

$$\tilde{J}(t) = \dfrac{J(t)}{1 + \alpha Z(t) + \beta Y(t)} + \dfrac{\alpha Z(t) + \beta Y(t)}{1 + \alpha Z(t) + \beta Y(t)} J_b$$

wherein:
J̃(t) is an optimal injection schedule adapted to physical activity at time t,
J(t) is an optimal injection schedule at time t,
Z(t) is the long-tem change in insulin sensitivity due to physical activity at time t,
Y(t) r represents the transient variation in metabolic activity at time t
$J_b$ injection needed to obtain the plasma concentration $I_b$,
β represents the short term metabolic demand to heart rate ratio, and
α is the long term change in amplitude.

* * * * *